(12) United States Patent
Margalit et al.

(10) Patent No.: US 7,544,374 B2
(45) Date of Patent: Jun. 9, 2009

(54) LIPIDATED GLYCOSAMINOGLYCAN PARTICLES AND THEIR USE IN DRUG AND GENE DELIVERY FOR DIAGNOSIS AND THERAPY

(75) Inventors: Rimona Margalit, Givatayim (IL); Dan Peer, Qiryat Ono (IL)

(73) Assignee: Tel Aviv University Future Technology Development L.P., Tel Aviv (IL)

( * ) Notice: Subject to any disclaimer, the term of this patent is extended or adjusted under 35 U.S.C. 154(b) by 567 days.

(21) Appl. No.: 10/487,022

(22) PCT Filed: Aug. 9, 2002

(86) PCT No.: PCT/US02/25178

§ 371 (c)(1),
(2), (4) Date: Jul. 19, 2004

(87) PCT Pub. No.: WO03/015755

PCT Pub. Date: Feb. 27, 2003

(65) Prior Publication Data

US 2004/0241248 A1    Dec. 2, 2004

Related U.S. Application Data

(60) Provisional application No. 60/379,741, filed on May 14, 2002, provisional application No. 60/311,849, filed on Aug. 14, 2001.

(51) Int. Cl.
*A61K 9/14* (2006.01)

(52) U.S. Cl. .................... 424/499; 424/489; 424/450

(58) Field of Classification Search .................. 424/499, 424/489, 450
See application file for complete search history.

(56) References Cited

U.S. PATENT DOCUMENTS

| 4,235,871 A * | 11/1980 | Papahadjopoulos et al. .. 424/450 |
| 4,898,735 A * | 2/1990 | Barenholz et al. .......... 424/450 |
| 4,902,512 A * | 2/1990 | Ishigami et al. ............ 424/450 |
| 4,927,637 A * | 5/1990 | Morano et al. ............. 424/450 |
| 5,143,713 A * | 9/1992 | Phillips et al. ............ 424/1.21 |
| 5,401,511 A | 3/1995 | Margalit |
| 5,614,506 A | 3/1997 | Falk et al. |
| 5,624,839 A | 4/1997 | Yada et al. |
| 5,639,738 A | 6/1997 | Falk et al. |
| 5,674,857 A | 10/1997 | Falk et al. |
| 5,733,892 A | 3/1998 | Sakurai et al. |
| 5,783,566 A * | 7/1998 | Mislick ...................... 514/44 |
| 5,792,753 A | 8/1998 | Falk et al. |
| 5,811,410 A | 9/1998 | Falk et al. |

(Continued)

OTHER PUBLICATIONS

Yagi, k. et al, Biochem. Molec. Biol. Internat. vol. 32, pp. 167-171 (1994).*

(Continued)

*Primary Examiner*—Gollamudi S Kishore
(74) *Attorney, Agent, or Firm*—Browdy and Neimark, PLLC

(57) ABSTRACT

Lipidated glycosaminoglycan particles are prepared by reacting a glycosaminoglycan with at least one lipid to cross-link the carboxylic acid groups in the glycosaiminoglycan with a primary amine in the lipid. These particles can be used to encapsulate active ingredients, such as drugs for use in the treatment of pathological conditions in an animal.

19 Claims, 21 Drawing Sheets

U.S. PATENT DOCUMENTS

| | | |
|---|---|---|
| 5,817,642 A | 10/1998 | Falk et al. |
| 5,824,658 A | 10/1998 | Falk et al. |
| 5,827,834 A | 10/1998 | Falk et al. |
| 5,830,882 A | 11/1998 | Falk et al. |
| 5,834,444 A | 11/1998 | Falk et al. |
| 5,847,002 A | 12/1998 | Willoughby et al. |
| 5,852,002 A | 12/1998 | Falk et al. |
| 5,910,489 A | 6/1999 | Falk et al. |
| 5,914,314 A | 6/1999 | Falk et al. |
| 5,914,322 A | 6/1999 | Falk et al. |
| 5,929,048 A | 7/1999 | Falk et al. |
| 5,932,560 A | 8/1999 | Falk et al. |
| 5,942,498 A | 8/1999 | Falk et al. |
| 5,962,433 A | 10/1999 | Falk et al. |
| 5,972,906 A | 10/1999 | Asculai et al. |
| 5,977,088 A | 11/1999 | Harper et al. |
| 5,985,850 A | 11/1999 | Falk et al. |
| 5,985,851 A | 11/1999 | Falk et al. |
| 5,990,095 A | 11/1999 | Falk et al. |
| 5,990,096 A | 11/1999 | Asculai et al. |
| 6,017,900 A | 1/2000 | Falk et al. |
| 6,022,866 A | 2/2000 | Falk et al. |
| 6,048,844 A | 4/2000 | Falk et al. |
| 6,069,135 A | 5/2000 | Falk et al. |
| 6,087,344 A | 7/2000 | Falk et al. |
| 6,103,704 A | 8/2000 | Falk et al. |
| 6,114,314 A | 9/2000 | Falk et al. |
| 6,136,793 A | 10/2000 | Falk et al. |
| 6,140,312 A | 10/2000 | Falk et al. |
| 6,147,059 A | 11/2000 | Falk et al. |
| 6,194,392 B1 | 2/2001 | Falk et al. |
| 6,218,373 B1 | 4/2001 | Falk et al. |
| 6,593,308 B2 | 7/2003 | Szoka, Jr. |
| 2002/0061849 A1* | 5/2002 | Nielsen et al. ............ 514/12 |
| 2002/0131995 A1* | 9/2002 | Szoka, Jr. ............... 424/450 |
| 2003/0175733 A1* | 9/2003 | Kirst et al. ................ 435/6 |

OTHER PUBLICATIONS

Firth, G. et al. Journal of the Neurological Science, vol. 63, pp. 153-165, 1984.*

* cited by examiner

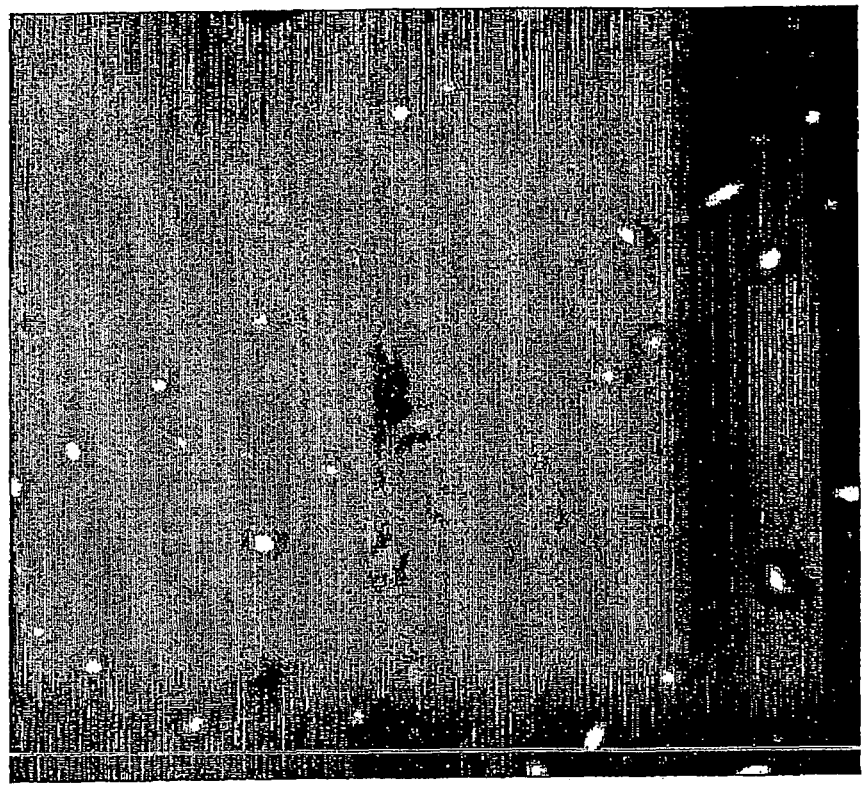
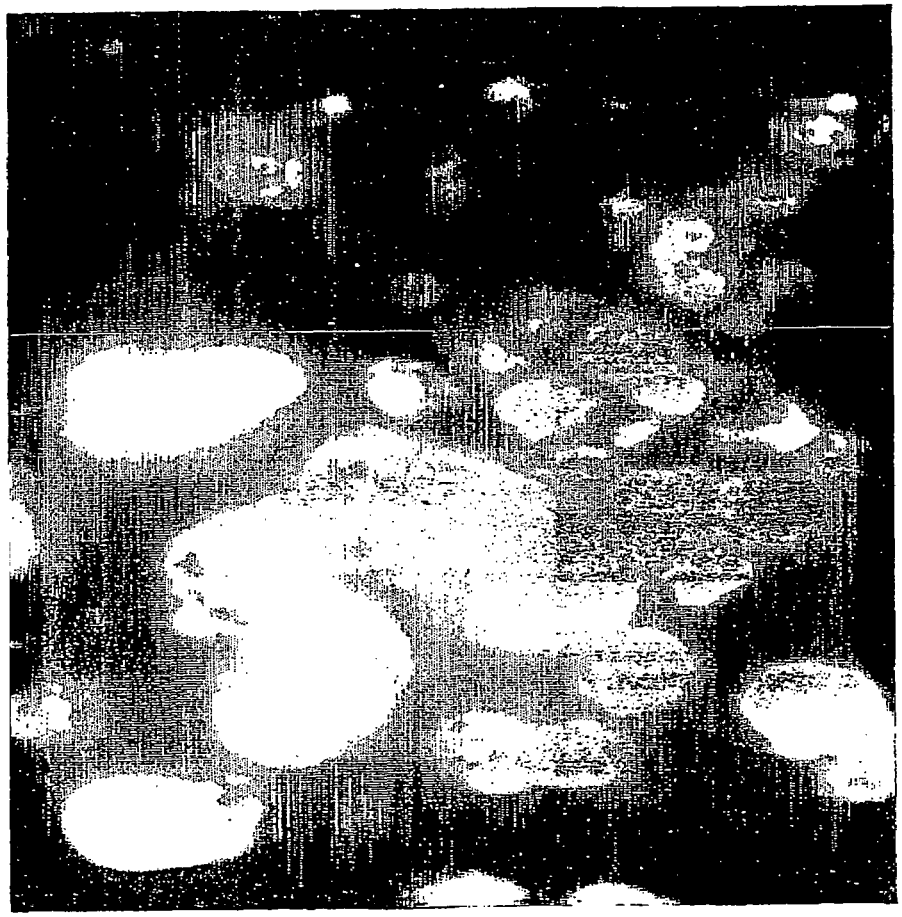

LIPIDATED GLYCOSAMINOGLYCAN PARTICLES AND THEIR USE IN DRUG AND GENE DELIVERY FOR DIAGNOSIS AND THERAPY

FIELD OF THE INVENTION

The present invention is directed to a drug delivery system based upon particles of lipidated glycosaminoglycans which encapsulate drugs for subsequent delivery for use in therapy and diagnosis.

BACKGROUND OF THE INVENTION

Glycosaminoglycans, or mucopolysaccharides, along with collagen, are the chief structural elements of all connective tissues. Glycosaminoglycans, or gags, are large complexes of polysaccharide chains associated with a small amount of protein. These compounds have the ability to bind large amounts of water, thereby producing a gel-like matrix that forms the body's connective tissues. Gags are long chains composed of repeating disaccharide units (aminosugar-acidic sugar repeating units). The aminosugar is typically glucosamine or galactosamine. The aminosugar can also be sulfated. The acidic sugar may be D-glucuronic acid or L-iduronic acid. In vivo, gags other than hyaluronic acid are covalently bound to a protein, forming proteoglycan monomers. The polysaccharide chains are elongated by the sequential addition of acidic sugars and aminosugars.

Among the most common gags are hyaluronic acid, keratan sulfate, chondroitin sulfate, heparin sulfate, and dermatin sulfate. Gags may be chemically modified to contain more sulfur groups than in their initially extracted form in addition, gags may be partially or completely synthesized and may be of either plant or animal origin.

Hyaluronic acid is a naturally occurring member of the glycosaminoglycan family which is present in particularly high concentration in the cartilage and synovial fluid of articular joints, as well as in vitreous humor, in blood vessel walls, and umbilical cord and other connective tissues. Hyaluronic acid can be in a free form, such as in synovial fluid, and in an attached form, such as an extracellular matrix component. This polysaccharide consists of alternating N-acetyl-D-glucosamine and D-glucuronic acid residues joined by alternating beta-1,3-glucuronidic and beta-1,4-glucosaminidic bonds. In water, hyaluronic acid dissolves to form a highly viscous fluid. The molecular weight of hyaluronic acid isolated from natural sources generally falls within the range of $5 \times 10^4$ up to $10^7$ daltons. Hyaluronic acid has a high affinity for the extracellular matrix and to a variety of tumors, including those of the breast, brain, lung, skin, and other organs and tissues.

A drug delivery system is used for maintaining a constant blood level of a drug over a long period of time by administering a drug into the body, or for maintaining an optimal concentration of a drug in a specific target organ by systemic or local administration, and over a prolonged period of time.

Chemically modified hyaluronic acid can be used for controlled release drug delivery. Balazs et al, in U.S. Pat. No. 4,582,865, state that "cross-linked gels of hyaluronic acid can slow down the release of a low molecular weight substance dispersed therein but not covalently attached to the gel macromolecular matrix."

Various forms of pharmaceutical preparations are used as drug delivery systems, including the use of a thin membrane of a polymer or the use of a liposome as a carrier for a drug.

There are two basic classes of drug carriers: particulate systems, such as cells, microspheres, viral envelopes, and liposomes; and non-particulate systems, which are usually soluble systems, consisting of macromolecules such as proteins or synthetic polymers.

Generally, microscopic and submicroscopic particulate carriers have several distinct advantages. They can perform as sustained-release or controlled-release drug depots, thus contributing to improvement in drug efficacy and allowing reduction in the frequency of dosing. By providing protection of both the entrapped drug and the biological environment, these carriers reduce the risks of drug inactivation and drug degradation. Since the pharmacokinetics of free drug release from the particles are different from directly-administered free drug, these carriers can be used to reduce toxicity and undesirable side effects.

Despite the advantages offered, there are some difficulties associated with using drug encapsulating biopolymers. For example, biopolymers structured as microparticulates or nanoparticulates have limited targeting abilities, limited retention and stability in circulation, potential toxicity upon chronic administration, and the inability to extravasate. Numerous attempts have been made to bind different recognizing substances, including antibodies, glycoproteins, and lectins, to particulate systems, such as liposomes, microspheres, and others, in order to confer upon them some measure of targeting. Although bonding of these recognizing agents to the particulate system has met with success, the resulting modified particulate systems did not perform as hoped, particularly in vivo.

Other difficulties have also arisen when using such recognizing substances. For example, antibodies can be patient-specific, and thereby add cost to the drug therapy. Additionally, not all binding between recognizing substrate and carrier is covalent. Covalent bonding is essential, as non-covalent binding might result in dissociation of the recognizing substances from the particulate system at the site of administration, due to competition between the particulate system and the recognition counterparts to the target site for the recognizing substance. Upon such dissociation, the administered modified particulate system can revert to a regular particulate system, thereby defeating the purpose of administration of the modified particulate system.

SUMMARY OF THE INVENTION

It is an object of the present invention to overcome the deficiencies in the prior art.

It is another object of the present invention to form glycosaminoglycan-based particles for encapsulating drugs.

It is another object of the present invention to deliver drugs encapsulated in a glycosaminoglycan-based particle.

It is a further object of the present invention to provide methods of drug delivery using particles of lipidated glycosaminoglycans as the drug delivery vehicles.

In a preferred embodiment, the delivery is by oral administration of the particle formulation. In another preferred embodiment, the delivery is by intranasal administration of the particle formulation, especially for use in therapy of the brain and related organs (e.g., meninges and spinal cord) that seeks to bypass the blood-brain barrier (BBB). Along these lines, intraocular administration is also possible. In another preferred embodiment, the delivery means is by intravenous (i.v.) administration of the particle formulation, which is especially advantageous when a longer-lasting i.v. formulation is desired.

It is still another object of the present invention to provide gene delivery using particles of lipidated glycosaminoglycans as the gene delivery materials.

The present invention provides a novel multi-product gene and drug delivery technology as well as methods of preparation and uses thereof. The delivery system comprises lipidated glycosaminoglycans, also known as gagomers, which are bioadhesive biopolymers produced by cross-linking a lipid having a primary amino group to a carboxylic acid-containing glycosaminoglycan. Micro- or nanoparticles are formed in a controlled manner, with dominant particle diameter ranges of about 2-5 microns for microparticles and about 50-200 nanometers for nanoparticles. Either small or large drugs, bioactive agents, or active ingredients such as antibiotics, chemotherapeutics, proteins, and nucleic acids can be entrapped in these particles with high efficiency, usually greater than 50%, even for large macromolecules. For example, for plasmid DNA the nanoparticles provide about 66% entrapment and the microparticles provide about 75% entrapment.

For purposes of the present invention, "drug" means any agent which can affect the body therapeutically, or which can be used in vivo for diagnosis. Examples of therapeutic drugs include chemotherapeutics for cancer treatment, antibiotics for treating infections, and antifungals for treating fungal infections. Examples of diagnostic drugs include radioactive isotopes such as. $^{99}Tc$, $^{127}I$, and $^{67}Gd$, and fluorescent molecules which are used in visualizing sites of interest in the body.

Preparation of the biopolymers of the present invention and drug entrapment are simple and cost-effective processes. These novel carriers act as sustained release drug depots, with half-lives in the range of 19-35 hours for the efflux of antibiotics and chemotherapeutics. These properties, together with their bioadhesive nature, provide these novel drug carriers the ability to perform as site-adherent, site-retained, sustained release drug depots for systemic, including oral, topical, and regional, including intranasal, administrations.

Additionally, the gagomers of the present invention are non-toxic. When chemotherapeutic drugs were entrapped and tested in a cell culture model, the systems exhibited high potential in tumor treatment, even overcoming the well known impediment of drug resistance. Thus, the gagomers can be used as microscopic and submicroscopic drug delivery systems for a wide range of therapeutic activities, such as cancer, infectious diseases, wound healing, enzyme therapy, gene therapy, and others.

Unexpectedly, the empty particles (containing only gagomers and no drug or other therapeutic formulation) also appear to have important tumor-inhibiting effects. Therefore, such particles may be useful for cancer therapy, especially for metastic cancer, either as a main or adjuvant chemotherapeutic agent.

BRIEF DESCRIPTION OF THE DRAWINGS

FIG. 1A is at 5000× magnification. FIG. 1B is at 3000× magnification.

FIG. 2A shows cells of the C6 (rat glioma) line that were incubated with a free ethidium bromide (EtBr). FIG. 2B shows cells of the C6 that were incubated with "empty" (i.e., entrapping buffer alone) gagomers suspended in a solution of free EtBr. FIG. 2C shows cells of the C6 that were incubated with EtBr-entrapping gagomers.

FIGS. 6A and 6B shows microscopy of microgagomers and nanogagomers. FIG. 6A shows fluorescent microscopy of micro-gagomers entrapping a model protein, BSA-FITC, magnification factor: 2000. FIG. 6B shows light microscopy of nanogagomers entrapping plasmid DNA, magnification factor: 2000.

DETAILED DESCRIPTION OF THE INVENTION

Figure 1A:
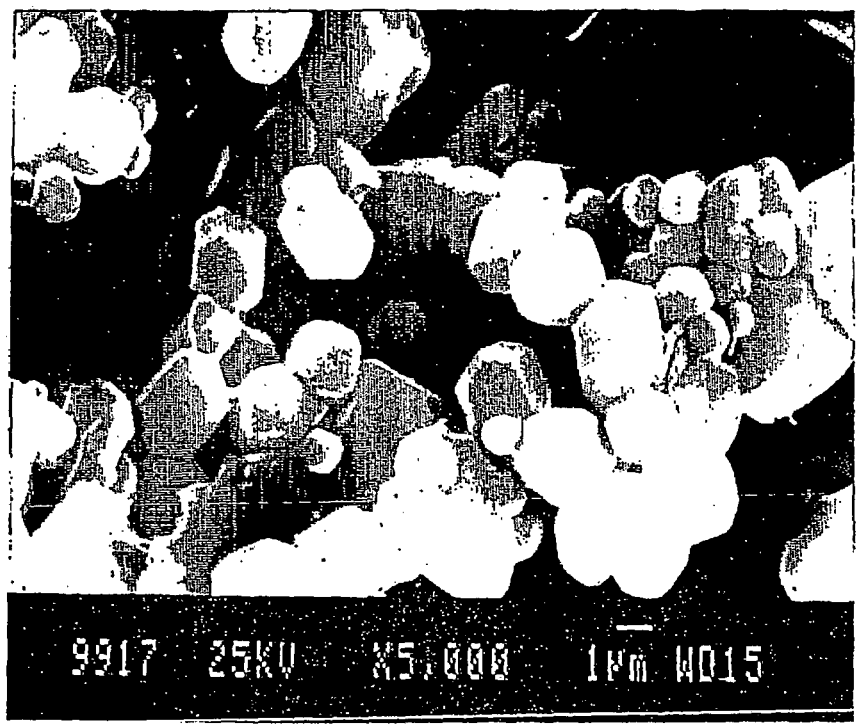
FIGS. 1A and 1B are scanning electron microscopy pictures of fields of particles from the same batch at two different magnifications.

The present invention relates to the preparation and uses of microscopic and submicroscopic delivery systems, as well as materials that can be used for tissue engineering and tissue scaffolding. The drug delivery systems of the present invention are novel adhesive biopolymers which take the form of a particulate carrier, also referred to as a gagomer, made from a lipid which contains at least one primary amine and a glycosaminoglycan, i.e., lipidated glycosaminoglycans.

The particles of the present invention are particularly cost-effective when compared to other particulate carriers, as shown in Table 1.

As used in the present application, the term hyaluronic acid, or HA, refers to hyaluronic acid and any of its hyaluronate salts, including, for example, sodium hyaluronate, potassium hyaluronate, magnesium hyaluronate, and calcium hyaluronate similarly, for any of the glycosaminoglycans, salts as well as free acids are included in the term glycosaminoglycan.

The gagomers of the present invention are microparticulate and nanoparticulate drug delivery systems, also referred to as MDDS and NDDS, respectively, that use drug-entrapping adhesive biopolymers. These carriers, when loaded with drugs, improve clinical outcomes compared to the same drugs administered in their free form. The gagomers are made from naturally-occurring materials which are bio-compatible and biodegradable.

TABLE 1

Advantages of Present Invention: Aspects of Cost-Effective Production

| Gagomers | Other Particulate Carriers |
|---|---|
| Cost-Effective Production: Raw Materials | |
| Stable, available, relatively inexpensive, fit a wide patient populations | Some or all components have stability and availability limitations, some may fit only narrow patient populations |
| Cost-effective Production: Manufacturing | |
| Manufacturing methodologies used for R & D are amenable to scale-up with little or no modifications | Most cases require large investment in developing scaled-up production methods |
| Cost-effective Production: Production Lines | |
| Since production of the lipidated-GAG and drug entrapment are separate processes, a single production line of the lipidated GAG fits all products. Two populations of particle sizes can be fractionated by a simple procedure, from the same batch. | Particle production and drug entrapment are done, for most, in the same process, requiring a separate product line for each final formulation. Likewise for different particle sizes. |
| Cost-Effective Production: Preparation of Formulation for Use | |
| Final formulation is by simple rehydration of the lipidated-GAG dry powder in an aqueous solution of the desired drug. Can be done at patient's bedside, home, etc. | The final formulation, including the entrapped drug, has to be provided by the manufacturer. |
| Cost-effective Production: Stability and Shelf Life | |
| Drug and lipidated-GAG can be stored separately in dry form, until reconstitution for use, providing high stability and long-term shelf life | Storage is of the final formulation, namely drug-loaded carrier. Dry form is not available in all cases. As a result there are limitations on both stability and shelf life |

The gagomers of the present invention have a number of other advantages over other particulate carriers, including aspects of their in vivo fate, as shown in Table 2.

TABLE 2

Advantages of Present Invention - Aspects of In Vivo Fate

| Gagomers | Other Particulate Carriers |
|---|---|
| In vivo Fate: Biodegradability and Biocompatibility | |
| All components are biomaterials, hence provide these properties | Some carriers have non-biological components that impair these properties |
| In Vivo Fate: Toxicity and Immunogenicity | |
| Based on nature of raw materials, no toxicity and low to no immunogenicity are expected. In vitro and in vivo studies confirm no toxicity. | Varies from one carrier to another. Acceptable in the few systems approved for clinical use. |
| In Vivo Fate upon i.v. Administration: Retention in Circulation | |
| Good and sufficient retention was confirmed as the GAG component already has the hydrophilic outer shell found | Poor and insufficient retention obtained, unless carrier is surface-modified to carry an appropriate ligand on |

TABLE 2-continued

Advantages of Present Invention - Aspects of In Vivo Fate

| Gagomers | Other Particulate Carriers |
|---|---|
| to delay opsonization and uptake by the RES. | its surface to delay both opsonization and uptake by the RES. |

The gagomers of the present invention also provide superior biological and therapeutic activity as compared with other particulate carriers. Some of these advantages are shown in Table 3.

TABLE 3

Advantages of Present Invention: Aspects of Biological/Therapeutic Activity

| Gagomers | Other Particulate Carriers |
|---|---|
| Biological/Therapeutic Activity: Efficiency of Drug Entrapment | |
| High-efficiency entrapment independent of drug size up to and including proteins and genetic material, due to a "wraparound" or "induced-fit" nature | Entrapment efficiencies run from poor to high, with low efficiency of high molecular weight entities |
| Biological/Therapeutic Activity: Site-Retention and Targeting | |
| The bioadhesive nature of the GAG component endows the systems with ability to adhere with high affinity to in vivo recognition sites and confers measures of active targeting | Further carrier modification, which is not always possible and in some cases is counter-productive to production and in vivo fate aspects, is required to endow the systems with these properties. |

Two basic type of gagomer may be synthesized: low lipid to glycosaminoglycan ratio, [1:1, w/w] denoted LLG, and high ratio of lipid to glycosaminoglycan, [5:1 to 20:1, w/w] denoted HLG. By changing specific steps in the preparation, the outcome can be directed to form micro- or nanoparticles.

The gagomers of the present invention, lipidated glycosaminoglycans, can be used as delivery systems for drug therapy to treat a pathological condition in an animal in need thereof. The term "animal" used herein is taken to include humans, and other mammals such as cattle, dogs, cats, rats, mice; as well as birds; reptiles; and fish.

For the present invention, pathological conditions suitable for treatment by means of the gagomers include but are not limited to cancer, fungal or bacterial infections, including those secondary to trauma such as burns, infections caused by parasites or viruses, prion infections, and the like.

The gagomers of the present invention may also have use in vaccine preparations and gene therapy. The preparation of vaccines containing an immunogenic polypeptide as the active ingredient is known to one of skill in the art. Likewise, the preparation of vectors for gene insertion is also known to one of skill in the art.

The gagomers formed by the procedures of the present invention may be lyophilized or dehydrated at various stages of formation. For example, the lipid film may be lyophilized after removing the solvent and prior to adding the drug. Alternatively, the lipid-drug film may be lyophilized prior to hydrating the gagomers. Such dehydration may be carried out by exposure of the lipid or gagomer to reduced pressure, thereby removing all suspending solvent.

Alternatively or additionally, the hydrated gagomer preparation may also be dehydrated by placing it in surrounding medium in liquid nitrogen and freezing it prior to the dehydration step. Dehydration with prior freezing may be performed in the presence of one or more protective agents, such as sugars. Such techniques enhance the long-term storage and stability of the preparations.

Following rehydration, the preparation may be heated. Other suitable methods may be used in the dehydration of the gagomer preparations. The gagomers may also be dehydrated without prior freezing. Once the gagomers have been dehydrated, they can be stored for extended periods of time until they are to be used. The appropriate temperature for storage will depend on the lipid formulation of the gagomers and temperature sensitivity of encapsulated materials.

When the dehydrated gagomers are to be used, rehydration is accomplished by simply adding an aqueous solution, such as distilled water or an appropriate buffer, to the gagomers and allowing them to rehydrate. This rehydration can be performed at room temperature or at other temperatures appropriate to the composition of the gagomers and their internal contents.

The gagomers of the present invention, lipidated glycosaminoglycans, are preferably prepared by covalently binding a lipid having at least one primary amino group to a carboxylic acid-containing glycosaminoglycan by the following method:

(a) A reaction vessel is provided in which the lipid is spread in a thin layer on the vessel bottom and walls. This can be effected by dissolving the lipid in an organic solvent and evaporating the lipid to dryness under low pressure in a rotary evaporator.

(b) The glycosaminoglycan is activated by pre-incubation in acidic pH with a crosslinker.

(c) The activated glycosaminoglycan is added to the reaction vessel.

(d) The reaction mixture of the lipid and activated glycosaminoglycan is buffered to a basic pH 8.6.

(e) The buffered reaction mixtures are incubated, with continuous shaking, for a period of time sufficient for the lipidated glycosaminoglycan to form, such as overnight at 37° C. Since the lipidated gags are designed to be used in vivo, they should be stable at about 37° C. While higher temperatures can be used for lipidation, lipids undergo physical changes with rising temperatures, generally about 62° C. Therefore, the lipidation preferably is conducted at temperatures from about 30-40° C.

(f) The lipidated glycosaminoglycan is buffered to a neutral pH and other ions and water-soluble additives are added according to need in order to elevate the ionic strength to physiological levels with ions or salts present in biological fluids (such as NaCl, KCl, $Ca^{2+}$ and $Mg^{2+}$)

(g) The particles are fractionated by successive centrifugations, each run at 4° C., for 40 minutes at the g force of $1.3 \times 10^5$, as follows: The pellet after 3 runs is the microparticle-enriched fraction, the supernatant of the microparticle enriched fraction subjected to 3 additional runs is the nanoparticle-enriched fraction.

(h) The resulting lipidated glycosaminoglycan is lyophilized.

To entrap drugs or other active ingredients in the gagomers, the material of interest is dissolved in ion-free pure water. The lyophilized dry powder gagomer obtained as above is then reconstituted in aqueous solution of the material to be entrapped.

Figure 5:
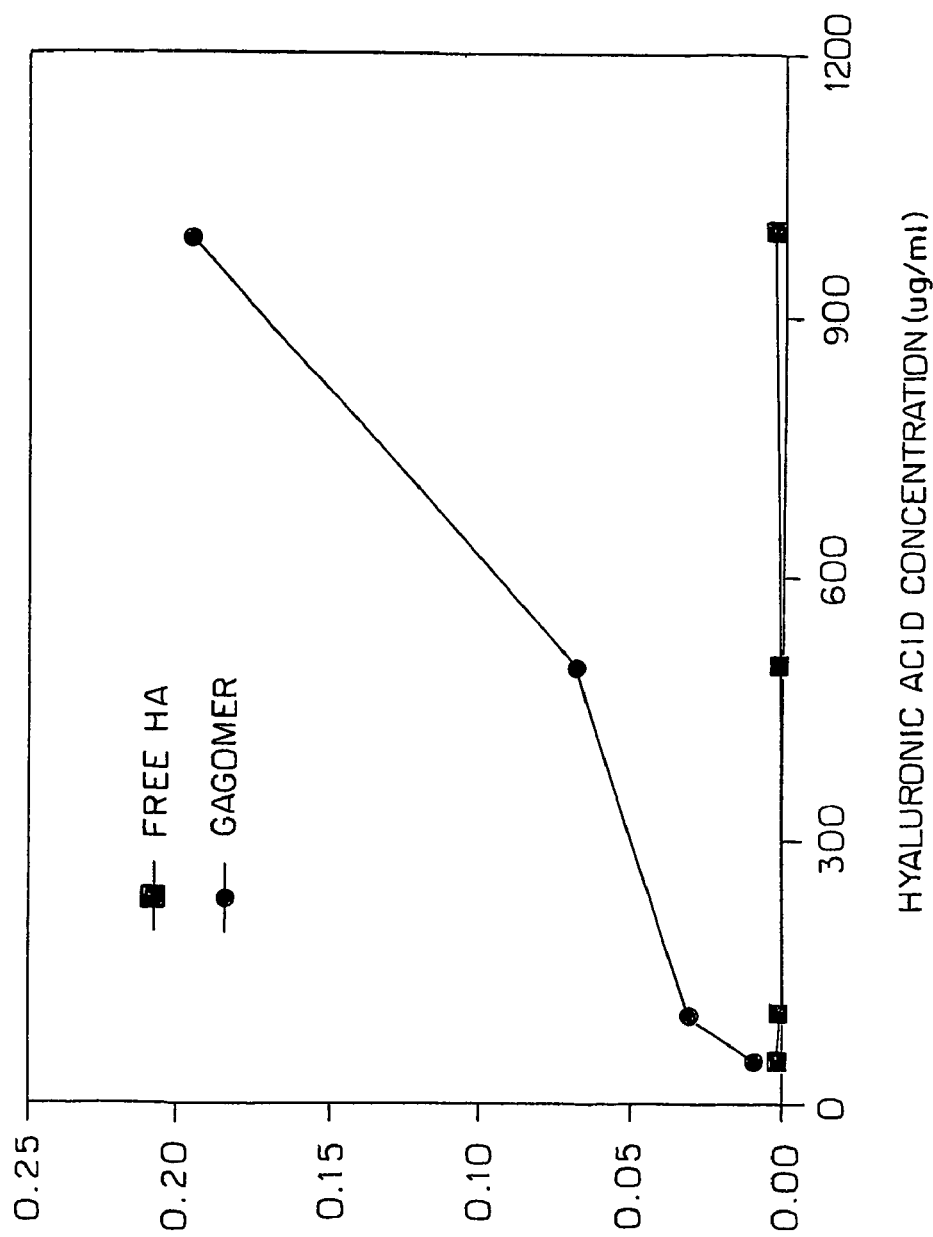
FIG. 5 shows the results of turbidity studies of free hyaluronic acid and a hyaluronic acid-based gagomer as a function of macromolecular concentration, following absorbency changes at 600 nm in the form of a graph plotting concentration of free hyaluronic acid and a hyaluronic acid-based gagomer.
Figure 7:
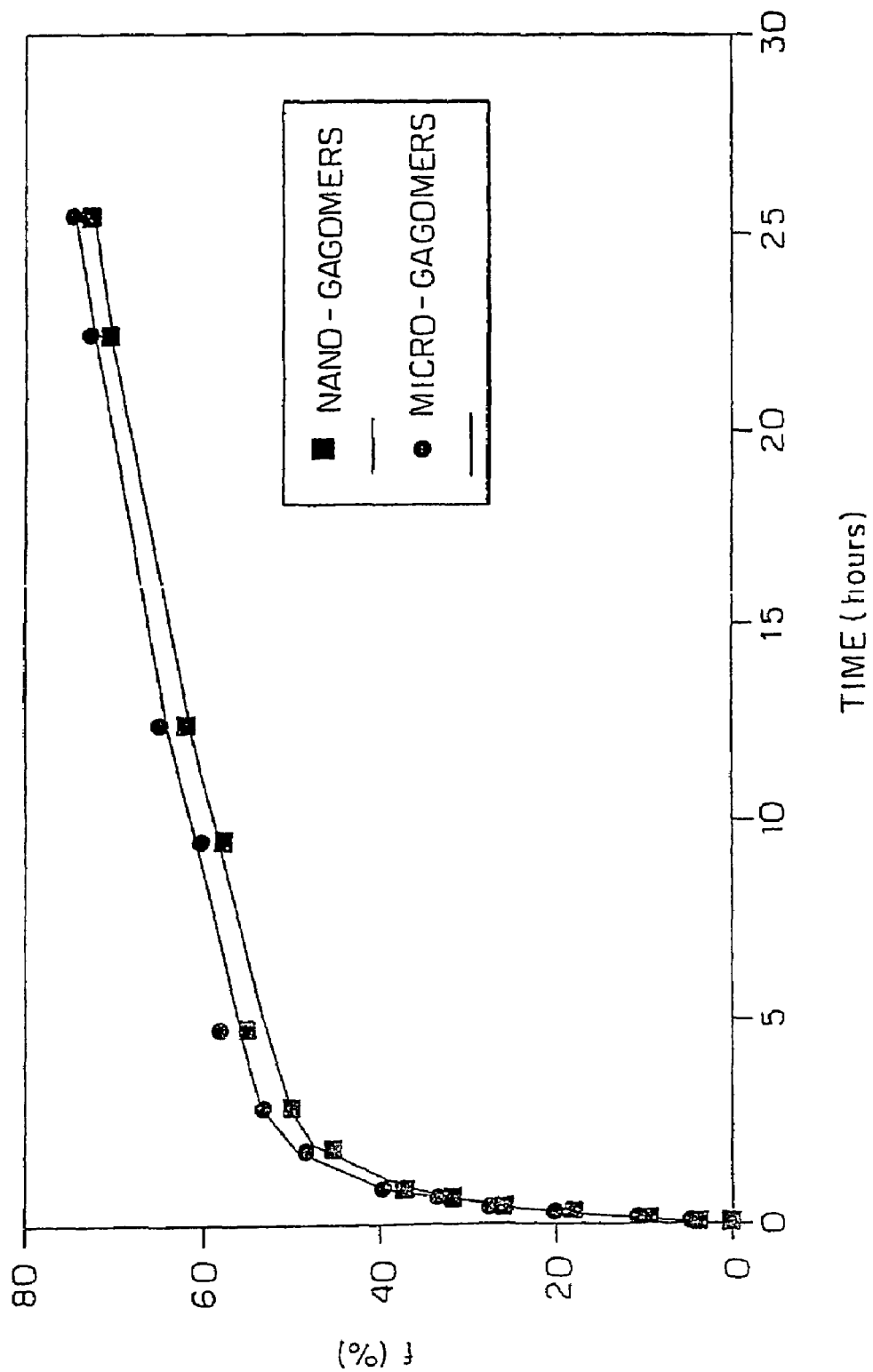
FIG. 7 is a graph illustrating doxorubicin efflux from micro (round) and nano (square) gagomers under conditions of unidirectional flux. The independent variable is time. The dependent variable (f) is the percentage of drug released at time=t with respect to the total drug in the system at time t=0. The symbols represent the experimental data and the solid curves are the theoretical expectations according to a multi-pool efflux mechanism.

Turbidity studies, following light scattering in a spectrophotometer, may be conducted for equal concentrations of soluble hyaluronic acid and of a gagomer prepared from hyaluronic acid and phosphatidylethanolamine to gain insight into whether the synthesis actually yields particulate matter. Representative results of such studies are shown in FIG. 5. As expected, over the concentration range tested free hyaluronic acid is soluble, and its solutions do not scatter light. In contrast, the gagomer-containing samples are turbid, the light scattering increasing with the gagomer concentration, making it clear that the biopolymer is an insoluble material.

Samples of the gagomers entrapping macromolecules are viewable both by light and by fluorescence microscopy. A typical field seen under the fluorescent microscope, of microparticles between 2 and 5 microns in diameter, prepared from HLG and entrapping a model protein, BSA-FITC, is shown in FIG. 6, top panel. These microparticles are prepared as described above. Prior to viewing under the microscope, the nonentrapped protein is removed from the preparation by ultracentrifugation at 4° C. for 30 minutes and a g force of $1.2 \times 10^5$. The pellet containing the particles with their entrapped protein is resuspended in phosphate buffered saline (PBS).

A typical field of nanoparticles (between 50 and 200 nm in diameter) seen under the light microscope prepared from HLG entrapping a plasmid DNA is shown in FIG. 6, bottom panel. The nanoparticles are prepared as described above for the FITC-BSA.

Particles made of glycosaminoglycans have a wide range of applications, as the same particles can be used alone, or with any type of material encapsulated therein. The glycosaminoglycan particles are preferably made without any encapsulated materials and then lyophilized to form a powder. The powdered glycosaminoglycan particles are then mixed with a powder of the material to be encapsulated. Alternatively, the powdered glycosaminoglycan particles are reconstituted by mixing with an aqueous solution of the material to be encapsulated. Once the mixture is reconstituted, the particles will have captured the material that was mixed in. Thus, small molecules, such as antibiotics and chemotherapeutic drugs, and large molecules, such as proteins, can be encapsulated with this technique. The particles can be used to encapsulate DNA, and the larger particles may even encapsulate whole cells and cell lines. Thus, the particles can also be used as a scaffold for tissue engineering.

The particles of the present invention are prepared by reacting at least one glycosaminoglycan in the long form, i.e., the gag has not been sliced up into smaller sizes. All glycosaminoglycans, except hyaluronic acid, are naturally in the form of a protein moiety bound covalently to a poly-saccharide moiety. Methods for hydrolyzing the protein-sugar bond are well known to those skilled in the art, both chemically and enzymatically. In addition, some commercial products are available in which the protein moiety has already been removed.

The glycosaminoglycan polymer is reacted with a lipid which has at least one primary amino group to cross-link the carboxylic residue of the glycosaminoglycan to a primary amine in the lipid. Once this reaction occurs, thermodynamic stability causes the lipids to interact with one another so as to pull the product into a sphere having the glycosaminoglycan on the outside and the lipids on the inside. These particles are then used to encapsulate other materials, including drugs, DNA, cells, proteins, etc.

In one embodiment of the present invention, the protein part of the glycosaminoglycan is removed and only the sugar backbone is reacted with the lipids.

It is known in the art to attach hyaluronic acid to the outside of liposomes for targeting or for making the liposomes more bioadhesive. In the instant invention, there is no liposome, rather, lipid molecules are attached covalently to hyaluronic acid.

In another embodiment of the present invention, other molecules may be attached first to the glycosaminoglycan, which is then reacted with lipids. These particles have the other molecules appearing on the outside of the particles. These other molecules may be, for example, antibodies, folate, porphyrins, or lectins, and may be used for targeting.

Although naturally-occurring glycosaminoglycans are preferred in the present invention in order to avoid problems with immunogenicity and toxicity, synthetic glycosaminoglycans can be used, as well as natural, synthetic, or semi-synthetic molecules, including but not limited to chondroitin, hyaluronic acid, glucuronic acid, iduronic acid, keratan sulfate, heparan sulfate, dermatin sulfate, and fragments, salts, and mixtures thereof. The term glycosaminoglycan as used herein further encompasses glycosaminoglycans that have been chemically altered (but not partially hydrolyzed), yet retain their function. These modifications include, but are not limited to, esterification, sulfation, polysulfation, and methylation.

Natural sources of glycosaminoglycans include both plant and animal sources, including but not limited to beechwood trees and forms of animal cartilage, including shark cartilage, bovine trachea, whale septum, porcine nostrils, and mollusks such as *Perna canaliculus* and sea cucumber.

It has been found that drugs encapsulated in the glycosaminoglycan particles of the present invention are much more effective than the free drugs, particularly for cancer cells that have become drug resistant. It appears that the gagomers attach to the cancer cells and thus become depots of drugs which can enter the cells more quickly than they are excreted. These drugs thus have a toxic effect on cells despite the drug-resistant mechanisms that have been developed, overwhelming the cancer cells.

The gagomers of the present invention can encapsulate almost any type of molecule without being modified. In contrast, liposomes, for example, must first be positively charged in order to complex with DNA, whereas liposomes encapsulating many other materials are not positively charged. It is an advantage of the present invention that the gagomers can encapsulate virtually any type of molecule.

The glycosaminoglycans are used at sizes obtained when they are purified from their biological sources, and that have not been subjected to chemical and/or biological degradation. For example, for hyaluronic acid, this corresponds to a range of about $1 \times 10^5$ to about $1 \times 10^7$ daltons.

Pharmaceutical compositions using gagomers according to the present invention can be administered by any convenient route, including parenteral, e.g., subcutaneous, intravenous, topical, intramuscular, intraperitoneal, transdermal, rectal, vaginal, intranasal or intraocular. Alternatively or concomitantly, administration may be by the oral route.

Parenteral administration can be by bolus injection or by gradual perfusion over time. Parenteral administration is generally characterized by injection, most typically subcutaneous, intramuscular or intravenous.

Topical formulations composed of the gagomer constructs hereof, penetration enhancers, and other biologically active drugs or medicaments may be applied in many ways. The solution can be applied dropwise from a suitable delivery device, to the appropriate area of skin or diseased skin or mucous membranes and rubbed in by hand or simply allowed to air dry. A suitable gelling agent can be added to the solution and the preparation can be applied to the appropriate area and rubbed in. For administration to wounds or burns, the gagomers may be incorporated into dosage forms such as oils, emulsions, and the like. Such preparations may be applied directly to the affected area in the form of lotions, creams, pastes, ointments, and the like.

Alternatively, the topical solution formulation can be placed into a spray device and be delivered as a spray. This type of drug delivery device is particularly well suited for application to large areas of skin affected by dermal pathologies, to highly sensitive skin or to the nasal or oral cavities. Optionally, the gagomers may be administered in the form of an ointment or transdermal patch.

Oral routes of administration are understood to include buccal and sublingual routes of administration.

The gagomers of the present invention may also be administered by other routes which optimize uptake by mucosa. For example, vaginal (especially in the case of treating vaginal pathologies), rectal and intranasal are preferred routes of administration. Further, the gagomers are particularly suited for delivery through mucosal tissue or epithelia. If administered intranasally, the gagomers will typically be administered in an aerosol form, or in the form of drops. This may be especially useful for treating lung pathologies. Suitable formulations can be found in *Remington's Pharmaceutical Sciences,* 16th and 18th Eds., Mack Publishing, Easton, Pa. (1980 and 1990), and *Introduction to Pharmaceutical Dosage Forms,* 4th Edition, Lea & Febiger, Philadelphia (1985), each of which is incorporated herein by reference.

Depending on the intended mode of administration, the compositions used may be in the form of solid, semi-solid or liquid dosage forms, such, as for example, tablets, suppositories, pills, capsules, powders, liquids, suspensions, or the like, preferably in unit dosage forms suitable for single administration of precise dosages. The pharmaceutical compositions will include the gagomer construct as described and a pharmaceutical acceptable excipient, and, optionally, may include other medicinal agents, pharmaceutical agents, carriers, adjuvants, etc. It is preferred that the pharmaceutically acceptable carrier be one which is chemically inert to the active compounds and which has no detrimental side effects or toxicity under the conditions of use. The choice of carrier is determined partly by the particular active ingredient, as well as by the particular method used to administer the composition. Accordingly, there are a wide variety of suitable formulations of the pharmaceutical compositions of the present invention.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders such as starch paste using, for example, maize starch, wheat starch, rice starch, potato starch, gelatin, tragacanth, methylcellulose, hydroxypropyl-methylcellulose, sodium carboxymethyl cellulose, and/or polyvinyl pyrrolidine.

Injectable formulations for parenteral administration can be prepared as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like such as for example, sodium acetate, sorbitan monolaurate, triethanolamine oleate, etc.

Aqueous injection suspensions may also contain substances that increase the viscosity of the suspension, including, for example, sodium carboxymethylcellulose, sorbitol, and/or dextran. Optionally, the suspension may also contain stabilizers.

The parenteral formulations can be present in unit dose or multiple dose sealed containers, such as ampules and vials, and can be stored in a freeze-dried (lyophilized) condition requiring only the addition of the sterile liquid carrier, e.g., water, for injections immediately prior to use. Extemporaneous injection solutions and suspensions can be prepared from sterile powders, granules, and tablets of the kind previously described.

For oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions include solutions, suspensions, tablets, dispersible tablets, pills, capsules, powders, sustained release formulations and the like. Formulations suitable for oral administration can consists of liquid solutions such as effective amounts of the compound(s) dissolved in diluents such as water, saline, or orange juice; sachets, lozenges, and troches, each containing a predetermined amount of the active ingredient as solids or granules; powders, suspensions in an appropriate liquid; and suitable emulsions. Liquid formulations may include diluents such as water and alcohols, e.g., ethanol, benzyl alcohol, and the polyethylene alcohols, either with or without the addition of a pharmaceutically acceptable surfactant, suspending agents, or emulsifying agents.

When the composition is a pill or tablet, it will contain, along with the active ingredient, a diluent such as lactose, sucrose, dicalcium phosphate, or the like; a lubricant such as magnesium stearate or the like; and a binder such as starch, gum acacia, gelatin, polyvinylpyrolidine, cellulose and derivatives thereof, and the like.

Tablet forms can include one or more of lactose, sucrose, mannitol, corn starch, potato starch, alginic acid, microcrystalline cellulose, acacia, gelatin, guar gum, colloidal silicon dioxide, crosscarmellose sodium, talc, magnesium stearate, calcium stearate, zinc stearate, stearic acid, and other preservatives, flavoring agents, and pharmaceutically acceptable disintegrating agents, moistening agents preservatives flavoring agents, and pharmacologically compatible carriers.

Capsule forms can be of the ordinary hard- or soft-shelled gelatin type containing, for example, surfactants, lubricant, and inert fillers, such as lactose, sucrose, calcium phosphate, and corn starch.

Lozenge forms can comprise the active ingredient in a carrier, usually sucrose and acacia or tragacanth, as well as pastilles comprising the active ingredient in an inert base such as gelatin or glycerin, or sucrose and acacia.

In determining the dosages of the gagomer particles to be administered, the dosage and frequency of administration is selected in relation to the pharmacological properties of the specific active ingredients. Normally, at least three dosage levels should be used. In toxicity studies in general, the highest dose should reach a toxic level but be sublethal for most animals in the group. If possible, the lowest dose should induce a biologically demonstrable effect. These studies should be performed in parallel for each compound selected.

Additionally, the ED50 (effective does for 50% of the test population) level of the active ingredient in question should be one of the dosage levels selected, and the other two selected to reach a toxic level. The lowest dose is that dose which does not exhibit a biologically demonstrable effect.

The toxicology tests should be repeated using appropriate new doses calculated on the basis of the results obtained.

Young, healthy mice or rats belonging to a well-defined strain are the first choice of species, and the first studies generally use the preferred route of administration. Control groups given a placebo or not treated are included in the tests. Tests for general toxicity, as outlined above, should normally be repeated in another non-rodent species, e.g., a rabbit or dog. Studies may also be repeated using alternate routes of administration.

Single dose toxicity tests should be conducted in such a way that signs of acute toxicity are revealed and the mode of death determined. The dosage to be administered is calculated on the basis of the results obtained in the above-mentioned toxicity tests. It may be desired not to continue studying all of the initially selected compounds.

Data on single dose toxicity, e.g., LD50, the dosage at which 50% of the experimental animals die, is to be expressed in units of weight or volume per kg of body weight and should generally be furnished for at least two species with different modes of administration. In addition to the LD50 value in rodents, it is desirable to determine the highest tolerated dose and/or lowest lethal dose for other species, i.e., dog and rabbit.

When a suitable and presumably safe dosage level has been established as outlined above, studies on the drug's chronic toxicity, its effect on reproduction, and potential mutagenicity may also be required in order to ensure that the calculated appropriate dosage range will be safe, also with regard to these hazards.

Pharmacological animal studies on pharmacokinetics revealing, e.g., absorption, distribution, biotransformation, and excretion of the active ingredient and metabolites are then performed. Using the results obtained, studies on human pharmacology are then designed.

Studies of the pharmacodynamics and pharmacokinetics of the compounds in humans should be performed in healthy subjects using the routes of administration intended for clinical use, and can be repeated in patients. The dose-response relationship when different doses are given, or when several types of conjugates or combinations of conjugates and free compounds are given, should be studied in order to elucidate the dose-response relationship (dose vs. plasma concentration vs. effect), the therapeutic range, and the optimum dose interval. Also, studies on time-effect relationship, e.g., studies into the time-course of the effect and studies on different organs in order to elucidate the desired and undesired pharmacological effects of the drug, in particular on other vital organ systems, should be performed.

The compounds of the present invention are then ready for clinical trials to compare the efficacy of the compounds to existing therapy. A dose-response relationship to therapeutic effect and for side effects can be more finely established at this point.

The amount of compounds of the present invention to be administered to any given patient must be determined empirically, and will differ depending upon the condition of the patients. Relatively small amounts of the active ingredient can be administered at first, with steadily increasing dosages if no adverse effects are noted. Of course, the maximum safe toxicity dosage as determined in routine animal toxicity tests should never be exceeded.

Compositions within the scope of the present invention include all compositions wherein the active ingredient is contained in an amount effective to achieve its intended purpose. While individual needs vary, determination of optimal ranges of effective amounts of each compound is within the skill of the art. The dosage administered will depend upon the age, health, and weight of the individual recipient thereof as well as upon the nature of any concurrent treatment and the effect desired. Typical dosages comprise 0.01 to 100 mg/kg body weight. The preferred dosages comprising 0.1 to 100 mg/kg body weight. The most preferred dosages comprise 1 to 50 mg/kg body weight.

The gagomers may be formulated to entrap therapeutic compositions for drug or gene therapy, or may be empty, for use in treating cancer, especially metastatic cancer.

EXAMPLE 1

Structural Studies of Micro-Gagomers

Figure 1B:
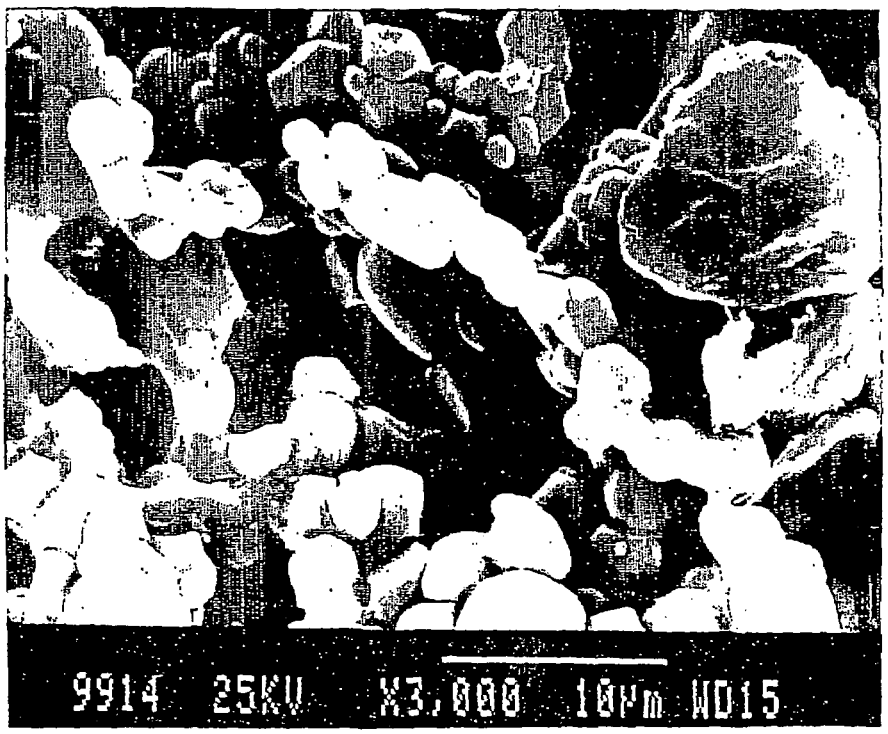

The structural data provided here (FIGS. 1A and 1B) was obtained by means of Scanning Electron Microscopy (SEM). Both parts of FIG. 1 are fields from the same batch, at two different magnifications (see information stamped by the device itself at the bottom of each figure). Three features are demonstrated by these results: (1) these data constitute a confirmation of the particulate nature of these polymers; (2) these data also constitute a confirmation of the size range (see 1 μm bar in FIG. 1A); and (3) some details are provided on the shape of the particles.

The particles are seen to be heterogeneous with respect to size. This is seen in FIG. 1A and more so in FIG. 1B. This is an expected outcome, since microscopy was done on the whole preparation, prior to fractionation into the nano- and microparticle populations. The magnification ranges applied under the microscope for use in SEM favor that of the microparticles.

EXAMPLE 2

Chemical Bonding

Since the lipid amino group was crosslinked to the carboxylic residues of hyaluronic acid, there should be a decline in the number of free carboxylic acids from free hyaluronic acid to the gagomer. The more lipid bound, the more extensive should be the decline of free carboxylic acid groups. Moreover, from the extent of free carboxylic acid loss, it is possible to measure the lipid to hyaluronic acid stoichiometry. Using a carboxylic acid assay, it was possible to measure the expected decline. It could also be estimated that, in the microparticles, about 33% of the glucuronic acid residues are occupied by lipid molecules, wherein in the nanoparticles only about 20% of the glucuronic acid residues are occupied by lipid molecules.

EXAMPLE 3

Physicochemical Details and Properties of the EtBr Gagomer Formulation

The efficiency of entrapment of drugs or other bioactive agents in the gagomers and the kinetics of drug efflux for small molecular weight drugs were determined using absorbency in an ELISA plate reader, with appropriate wavelengths for each given entrapped entity.

Typical results of the efficiency of entrapment are shown in Tables 4 and 5 of the microparticles and nanoparticles, respectively.

TABLE 4

Micro-Gagomers: Efficiency of Drug Entrapment and Half-Life of Drug Efflux

| Entrapped Entity | Encapsulation Efficiency (%) | | Half-Life of Drug Efflux (Hours) |
|---|---|---|---|
| | By Thermodynamics | By Kinetics | |
| Fluorescein | 49.6 ± 4.8 | 40.6 ± 5.8 | 7.9 |
| Chloramphenicol | 39.3 ± 3.9 | 30.5 ± 1.9 | 28.2 |
| Mitomycin C | 49.4 ± 2.5 | 44.3 ± 2.7 | 20.1 |
| Doxorubicin | 52.4 ± 6.3 | 50.2 ± 1.2 | 35.3 |
| BSA | 32.0 ± 2.5 | | |
| DNA | 74.5 ± 2.8 | | |

TABLE 5

Nano-Gagomers: Efficiency of Drug Entrapment and Half-Life of Drug Efflux

| Entrapped Entity | Encapsulation Efficiency (%) | | Half-Life of Drug Efflux (Hours) |
|---|---|---|---|
| | By Thermodynamics | By Kinetics | |
| Fluorescein | 37.4 ± 1.2 | 29.1 ± 6.1 | 21.9 |
| Chloramphenicol | 47.4 ± 0.3 | 47.1 ± 1.5 | 14.8 |
| Mitomycin C | 54.8 ± 0.9 | 41.7 ± 1.6 | 29.8 |
| Doxorubicin | 57.0 ± 3.7 | 53.6 ± 0.9 | 22.3 |
| BSA | 35.0 ± 1.8 | | |
| DNA | 65.8 ± 4.8 | | |

The concentration of gagomer-entrapped EtBr was 25 µM. Efficiency of entrapment was 49.8(±3.1) (%). Half-life of EtBr efflux from the gagomer was 27.7 hours.

EXAMPLE 4

In Vitro Toxicity Studies

Drug-free gagomers of both micro- and nano-size ranges, were tested for toxicity in cell cultures for both low lipid and high lipid gagomers. Two cell lines were tested, the rat glioma cell line C6 and the mouse fibroblast line NIH3T3. In all cases the gagomers were found to have no toxicity over the 100-fold concentration range of 0.02 to 2 mg/ml polymer.

EXAMPLE 5

Therapeutic Activity Exemplified by Treatment of a Drug-Resistant (MDR) Glioma Cell Line Due to their location and poor response to chemotherapeutic drugs, brain tumors, particularly gliomas, are very difficult to treat (Wolff et al, 1999; Nutt et al, 2000. The poor drug response is due in part to lack of access and in part to inherent multidrug resistance (MDR) of these tumors (Larsen, 2000; Gottesman et al, 1995).

In brain tumors, multidrug resistance is an impediment even in cases where access to the tumor has been provided, such as by local administration or leaving a local depot at the end of a surgical procedure. In this prevalent drug resistance mechanism, which appears in both an acquired and inherent mode, the drugs do not lose their intrinsic toxic activity, nor have the resistant cells found a way to metabolize the drugs to nontoxic entities. Rather, the drug that enters the cell through passive diffusion across the cell membrane is actively pumped out, reducing intracellular levels to below their lethal threshold. The glioma C6 line, which displays inherent MDR, served as the model system for testing whether treatment with gagomers encapsulating a chemotherapeutic drug would offer any advantage over a similar treatment with the free drug.

Methodology

Cells were seeded onto 96 well plates, and the experiment was initiated at semi-confluency, usually 24 hours post seeding. The cells were given a selected dose of the drug of choice, entrapped in a gagomer formulation that was washed of excess nonentrapped drug prior to use. Control systems were the same dose of free drug, and a dose of drug-free gagomer at a dose similar to that of the test system. Cell survival was determined 48 hours post-treatment, using the MTT assay (Nutt et al, 2000; Larsen et al, 2000).

Results

Figure 8:
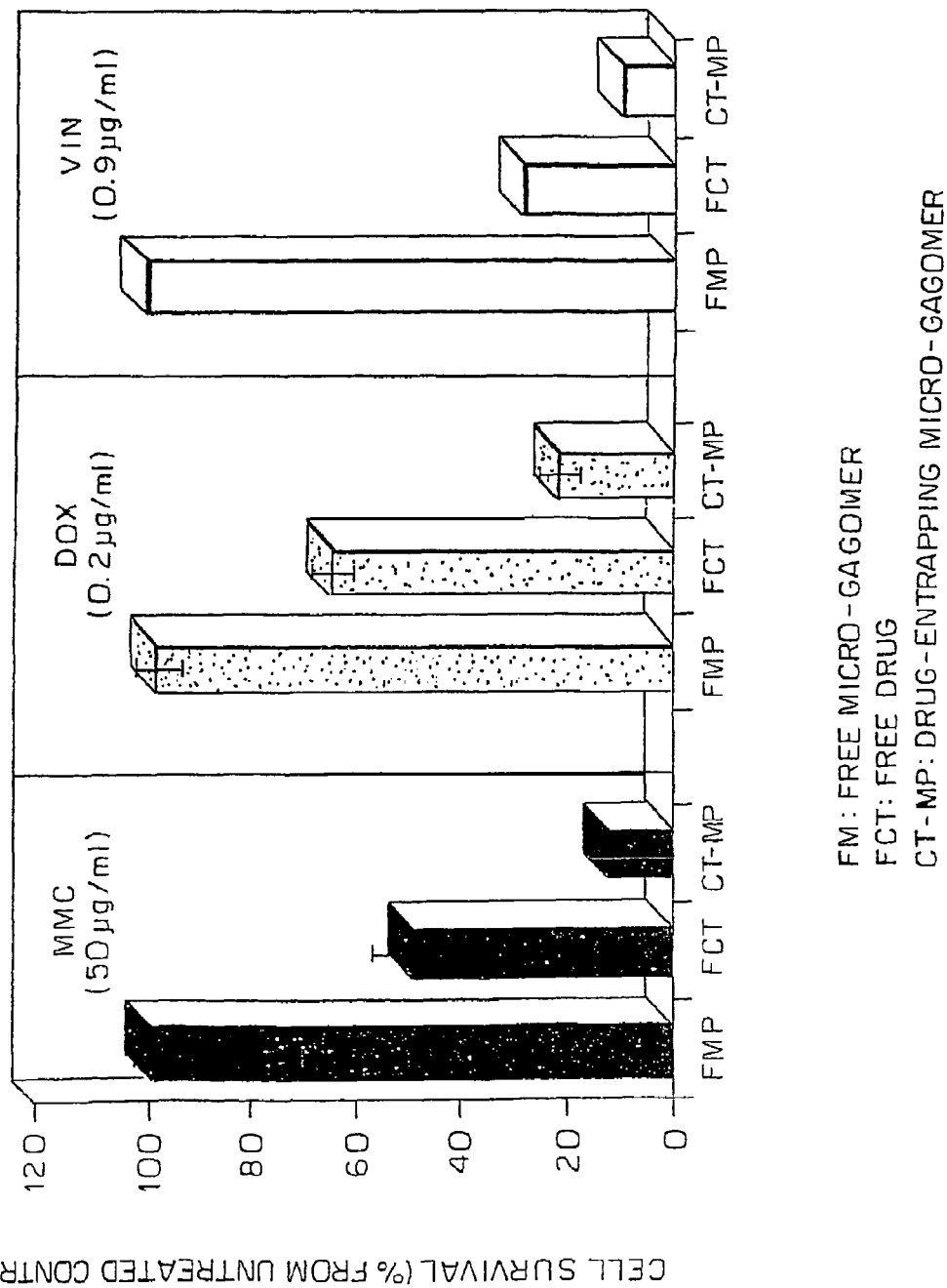
FIG. 8 is a graph showing survival of C6 cells 48 hours post-treatment by free micro-gagomer (i.e., encapsulating buffer alone, as in "empty" defined in the description to FIG. 2B), a given dose of a free chemotherapeutic drug, and an equivalent dose of the same drug entrapped in the micro-gagomer. The studies were conducted with mitomycin c (MMC), doxorubicin (DOX), and vinblastine (VIN), and the results are organized into three data sets, one for each drug. Each bar is an average of three independent experiments, each of which comprised 20 separate measurements. The error bars represent the respective standard deviations.

Results for three chemotherapeutic drugs are shown in FIG. 8 in three data sets. The data for the free gagomer (left-most bar in each of the three data sets) is an additional confirmation of the data discussed above with respect to the gagomers being non-toxic. Depending upon the specific drug, with each drug operating at its own dose range, it can be seen that even relatively high doses of free drug permit 20-60% of the cells to survive. Such results, shown in the middle bar of each data set, are typical for the inherent form of multidrug resistant cells. Replacing the free drug with the same dose of gagomer-entrapped drug generated a dramatic differences as can be seen by the right-most bar in each data set. For each of the three drugs, the novel formulation generates a 3-4-fold increase in cell death as compared to the corresponding free drug. Two findings tightly link this improved response in treatment to the novel drug delivery formulation of the present invention: the non-toxic nature of the free gagomer, and the increased cell demise obtained for three different drugs that each have a unique cytotoxic mechanism.

To overcome multidrug resistances a mechanism must be found to elevate intracellular doses of a chemotherapeutic drug above the lethal threshold. The traditional approach taken in the attempt to achieve this elevation is to reduce the pumping by using reversal agents that are also known as chemosensitizers. While several of these agents have been identified, most prominent among them verapamil, none of the currently available chemosensitizers can be used clinically. In addition, treatment requires careful orchestration, as the two active entities, the chemotherapeutic drug and the chemosensitizers, must reach the target together to be effective. This is not a simple matter in clinical practice.

Another way to elevate intracellular drug dose is to increase influx, both in-magnitude and duration. It appears that the outstanding increase in drug response for the drug-entrapping gagomers of the present invention operates by increasing influx. The bioadhesive nature of the gagomers positioned them as drug depots bound to the cell membrane. This both increased the electrochemical gradient of the drug across the cell membrane as compared to the free drug, as well as the time span during which drug entry occurs. Thus, treatment only requires one entity, the drug-gagomer composition. These new formulations will also benefit non-resistant tumors by allowing successful treatment with significantly lower drug doses.

EXAMPLE 6

Interaction of Micro-Gagomers with Cells

Cells are known to be impermeable to EtBr (ethidium bromide), a nucleic-acid sensitive fluorescent marker. Its fluorescence emission is significantly enhanced upon binding to DNA and RNA, allowing for determination of whether a carrier has made cells permeable to EtBr and, in particular, whether it has reached the nucleus.

In order to probe the interactions of these novel polymers with cells EtBr-encapsulating gagomers were prepared, the physicochemical properties of these gagomers were determined, and then the gagomers were incubated with cells. The results were scanned using confocal microscopy.

Two cell lines were tested, C6—a rat glioblastoma cell line, and PANC-1—a human pancreatic adenocarcinoma cell line. For each cell line, monolayers of the cells were incubated with three different formulations: (1) free EtBr, (2) "empty" (i.e. encapsulating buffer alone) gagomers suspended in a solution of free EtBr, and (3) EtBr-entrapping gagomers.

In all three formulations the EtBr was used at the same 2.5 $\mu$M concentration. The gagomers in formulations (2) and (3) were at the same concentration—0.25 mg/ml. Each formulation was incubated with the cells for 60 minutes at room temperature, prior to performance of the confocal microscopy. The results are shown in FIG. 2 for the cell line C6 and in FIGS. 3 and 4 for the cell line PANC-1.

Figure 2A:
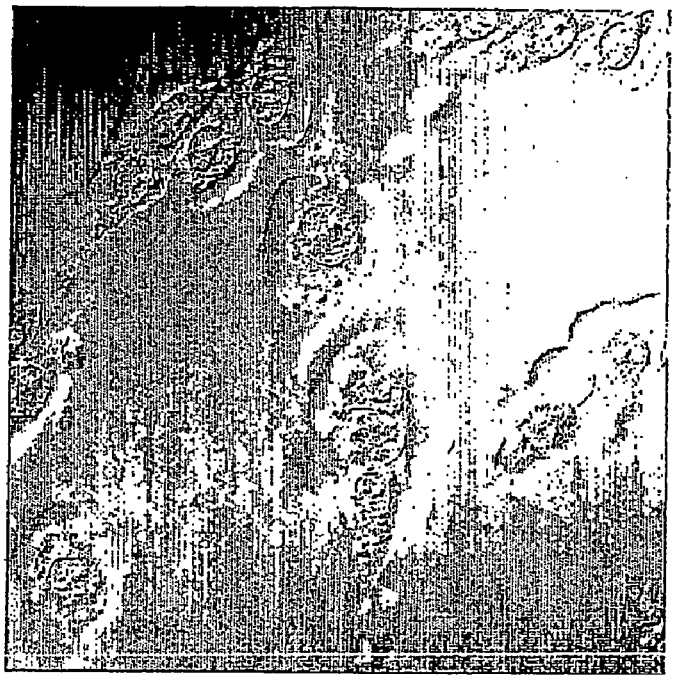
FIGS. 2A-2C are confocal micrographs showing individual cells incubated with three different formulations.
Figure 2B:
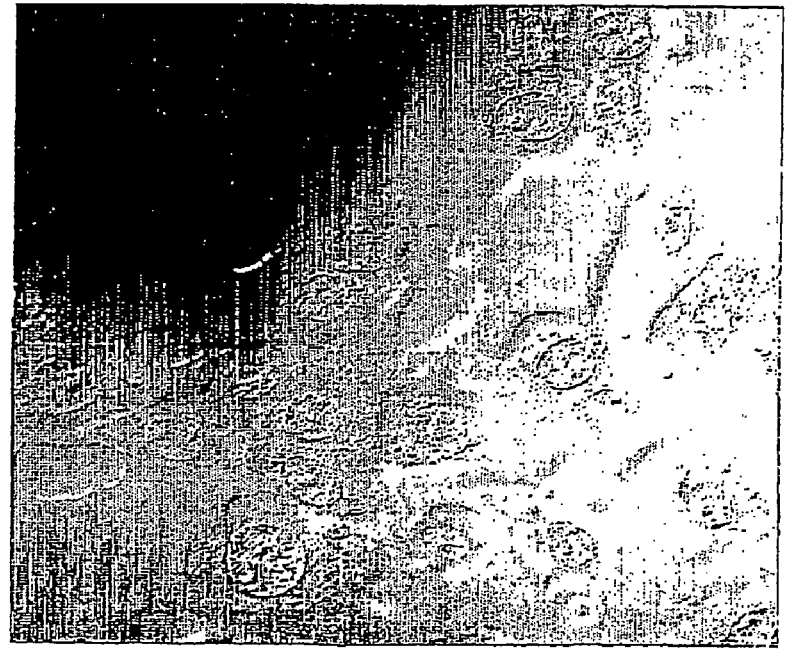
Figure 2C:
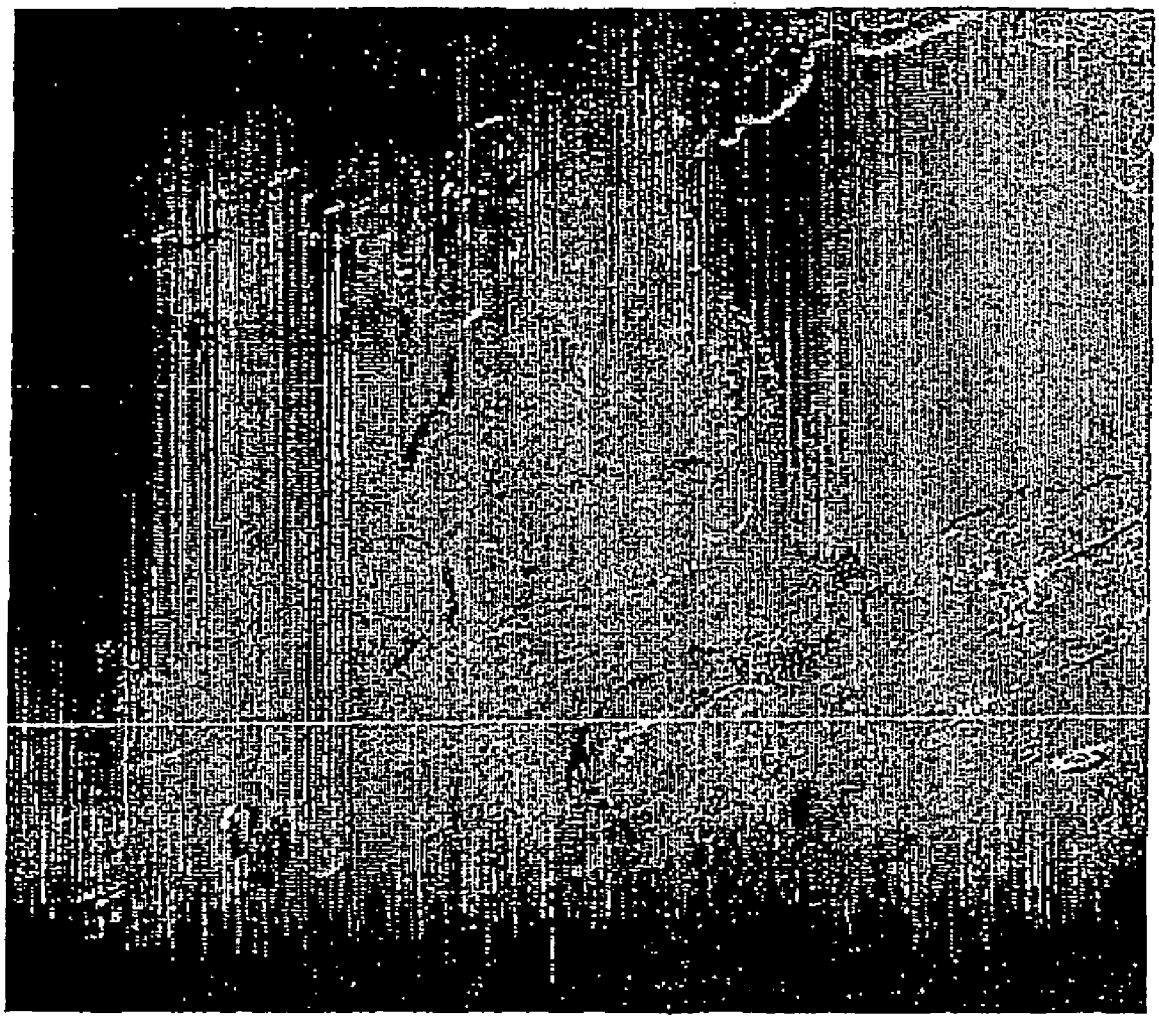

The results for the C6 cell line is shown in FIG. 2A. The upper left section shows results of cells incubated with free EtBr. It is clear that there is negligible fluorescence inside the cells, as expected for this marker when it is free in solution. The upper right section of FIG. 2A is for the cells incubated with free EtBr in a solution that had empty gagomers suspended in it. Negligible fluorescence is seen here, and its similarity to free EtBr is a clear indication that the particles themselves do not promote entry of free (non-entrapped) EtBr into the cells.

In contrast to these two controls, when the EtBr is entrapped inside the particle, it gains entry into the cells and into the nucleolus. This is clear from the high fluorescence intensity of the bottom part of FIG. 2A, and from its localization inside the cells inside the nucleolus (interacting with DNA) and also in the cytosol (interacting with RNA). These findings are not restricted to a specific cell line, as similar results were obtained with the PANC-1 line also.

Figure 3A:
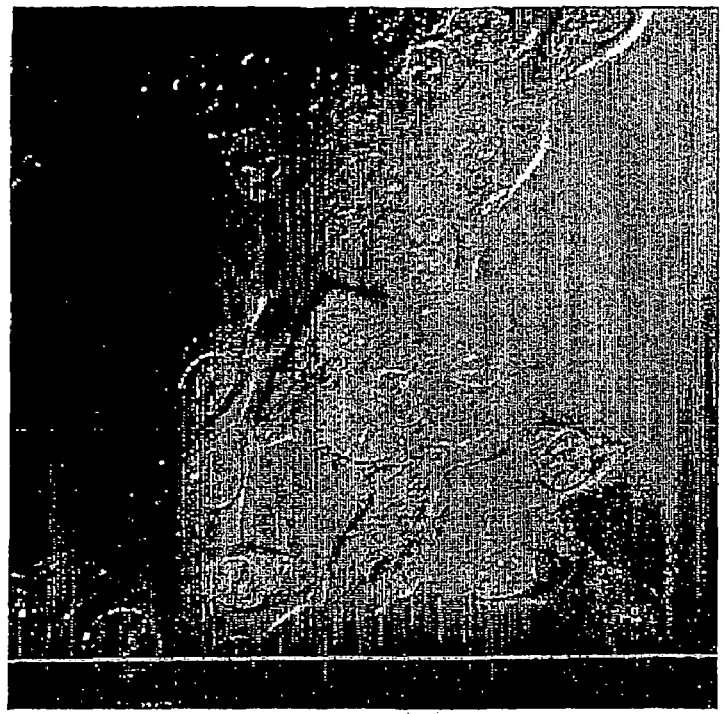
FIG. 3A shows cells of the PANC-1 cell line (from human pancreatic adenocarcinoma) treated with gagomer-encapsulated EtBr.
Figure 3B:
FIG. 3B shows cells of the PANC-1 cell line treated with free EtBr.
Figure 4A:
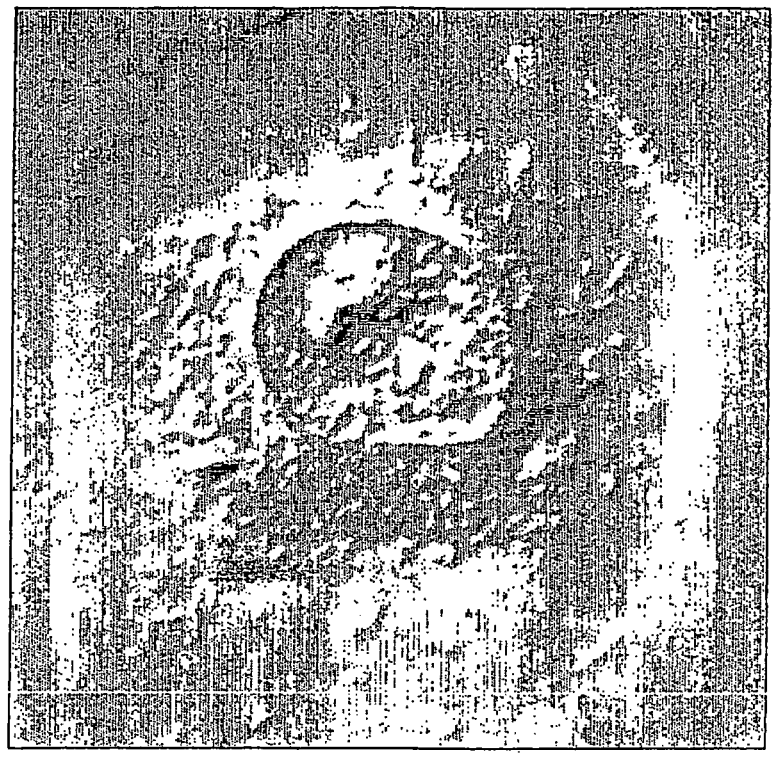
FIG. 4A is a confocal micrograph of a system similar to FIG. 3B, but at a larger magnification.
Figure 4B:
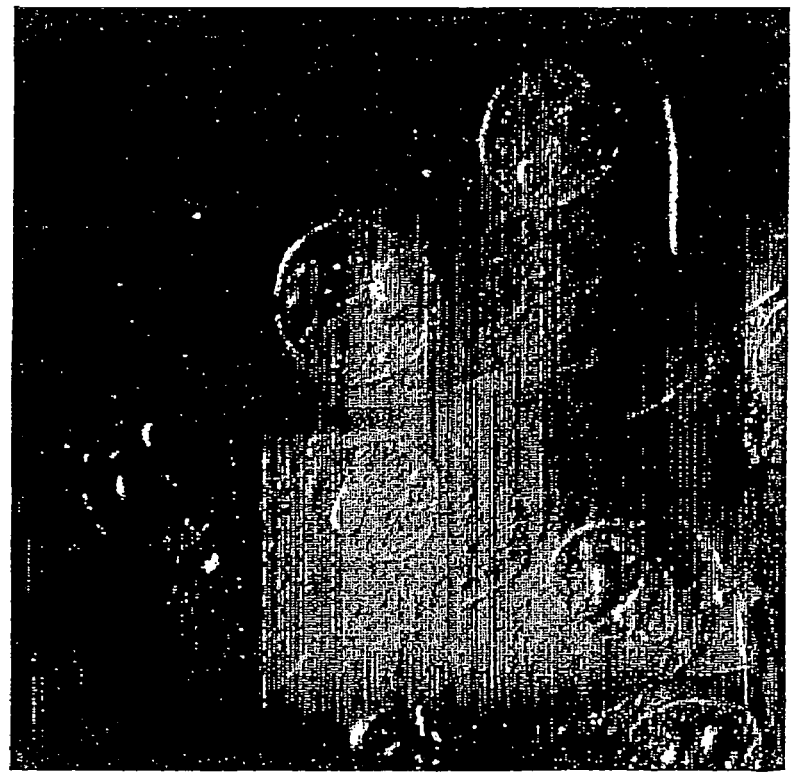
FIG. 4B is a confocal micrograph of a system similar to FIG. 3A, but at a larger magnification.

In FIG. 3 the results with formulations (2) and (3) alone are depicted. The sizeable differences between free and gagomer-entrapped EtBr are shown in greater detail in FIG. 4. FIG. 4A shows a single cell incubated with free EtBr. Only a negligible amount of the marker has entered the cell and reached the nucleolus. Also, if there is any EtBr in the cytosol it is below detection. In contrast, as shown in FIG. 4B, when incubated with gagomer-entrapped EtBr, substantial amounts of the marker enter the cell and are found in the nucleus (DNA-bound) and in the cytosol (RNA-bound).

As all data were obtained using the same concentration of EtBr, it seems clear that the entrapment within the polymer made the difference. In principle, there are three major mechanisms that can account for a carrier facilitating entry of its nucleic acid-sensitive marker load into a cell in such a manner that allows free intracellular marker to interact with RNA and also gain entry into the nucleolus to interact with the DNA:

(1) Adsorption and Diffusion. The marker-loaded particles adhere to the cell membrane, creating local depots. Marker diffuses out of the adhering particles and some of this freed marker diffuses across the cell membrane, into the cell.

(2) Fusion. The marker-loaded carrier first binds to the cell membrane, then fuses with it and in the course of fusion, entrapped material is released into the cytosol.

(3) Endocytosis and Release. The marker-loaded carrier enters the cell by an endocytotic pathway. The endocytosed carrier succeeds in releasing marker into the cytosol. In all three mechanisms, once the marker is free in the cytosol, part of this now-intracellular marker pool finds its way to the nucleolus.

The first mechanism may be eliminated on account of physicochemical data showing efflux of the entrapped marker to be quite slow. Based on the efflux rate constant (listed above in the form of half-life), it can be calculated that in the course of the 50 minutes incubation prior to the microscopy, efflux would be at the most 2% of the entrapped marker, corresponding to 0.5. $\mu$M EtBr becoming free. Even if all of this were to get across the cell membrane into the cell, the result would have been even more negligible than seen with the 50 fold higher concentration (25 $\mu$M vs. 0.5 $\mu$M) of free EtBr (FIG. 2A). In contrast, the results with the carrier-entrapped marker show a substantially higher entry such as could not be obtained through the "adsorption and diffusion" mechanism.

Regardless of whether the fusion or endocytotic mechanism of treatment of cancer cells is the means by which entrapped marker enters the cell, it is clear that this carrier allows impermeable molecules into the cell and into the nucleolus. This ability bodes well for performance of the gagomers in drug delivery.

EXAMPLE 7

Formulation Studies

Particle Properties

Sizing the Particles: The low lipid to glycosaminoglycan ratio (LLG) and high lipid to glycosaminoglycan ratio (HLG) nano- and microparticles were sized using an ALV-NIBS particle sizer. The results, listed in Table 6, provide full quantitative data and are in good agreement with the previously-obtained microscopy data (EM, fluorescence). The two sizes are well distinguished from one another, and the relatively low scatter within each system indicates good efficiency of the separation process. The data also show that within each particle type, there is some flexibility in designing particle size through manipulation of the lipid/HA ratio.

TABLE 6

Size Distributions of the Nano and Micro Tau DDS Systems

| Particle Specifications | | Particle Diameter |
|---|---|---|
| Type | Lipd/HA Ratios | (nm) |
| Nano | LLG | 227 ± 37 |
|  | HLG | 135 ± 41 |
| Micro | LLG | 1330 ± 225 |
|  | HLG | 1150 ± 178 |

Figure 9:
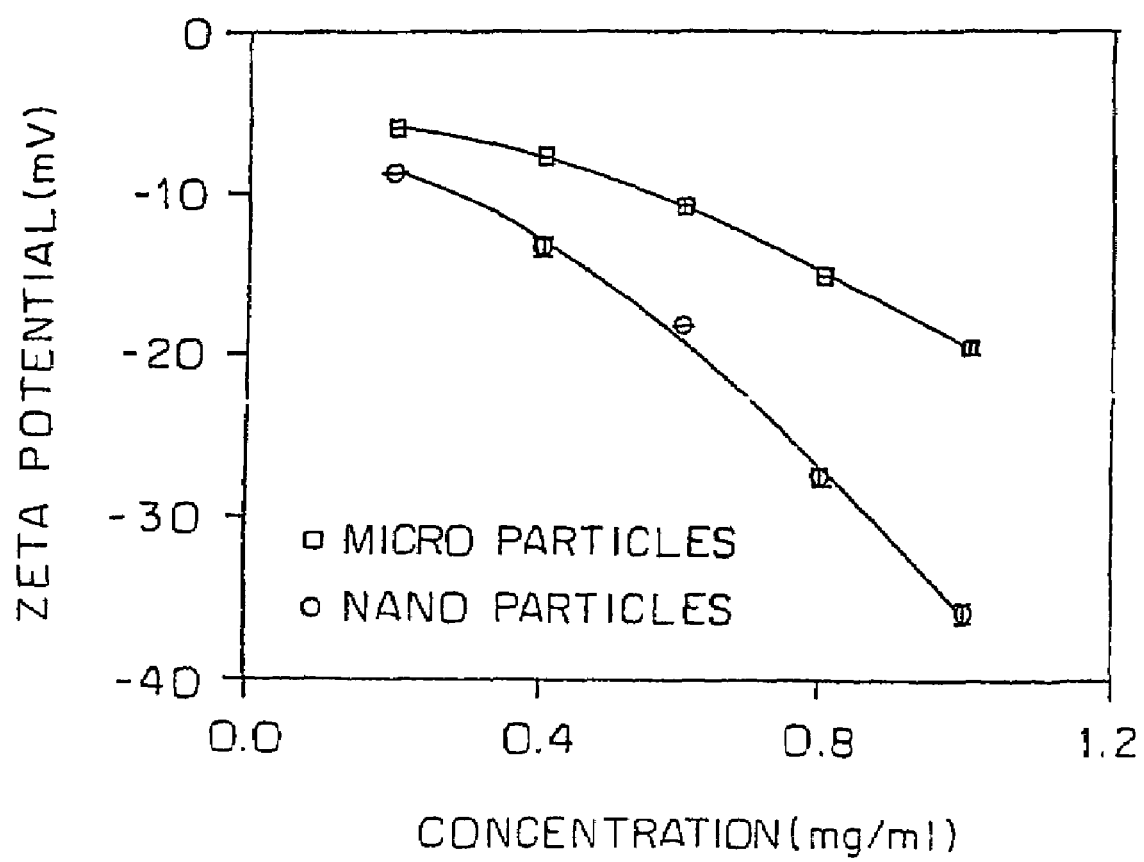
FIG. 9 shows the zeta potentials (effective surface charge) of the nano- and microparticles as a function of concentration. Zeta potentials reflect the total interaction forces between colloidal size particles in suspension.

Zeta Potentials: The zeta potentials of both micro- and nanoparticles were measured, as a function of particle concentration. The zeta, or electrokinetic potential represents the potential across the diffuse layer of ions surrounding any charged colloidal particle, and is largely responsible for colloidal stability. Typical results, shown in FIG. 9, demonstrate that: (a) as expected on the basis of particle chemical composition and particle structural features, the zeta potentials are negative; and (b) the patterns observed for the dependence of zeta potential on concentration fit with the general pattern observed in the field for negatively charged particles.

Entrapment Efficiencies

Two formulations were investigated: insulin and α-interferon, each entrapped in separate formulations in the microparticles. The entrapment efficiencies obtained are shown in Table 7. Clearly, both new proteins are entrapped with high efficiency, as was previously shown for other macromolecules (Tables 4 and 5). The insulin concentration was 10 mg/ml. At this range this protein is already aggregated into dimers and hexamers, meaning that the entities entrapped were larger than 6000 da. Levels of encapsulation this high, at this level of insulin doses, were not reported for other particulate carriers.

TABLE 7

Encapsulation Efficiencies of Therapeutic Proteins in the Novel DDS (Microparticles)

| Encapsulated Matter | MW Range (Da) | Encapsulation Efficiency (%) |
|---|---|---|
| Insulin (Human Recombinant) | 6,000 | 86.9 ± 4.7 |
| α-Interferon (Human Recombinant) | 19,000 | 72.5 ± 3.7 |

EXAMPLE 8

In Vitro Studies

Toxicity Testing in Cell Cultures

Figure 10:
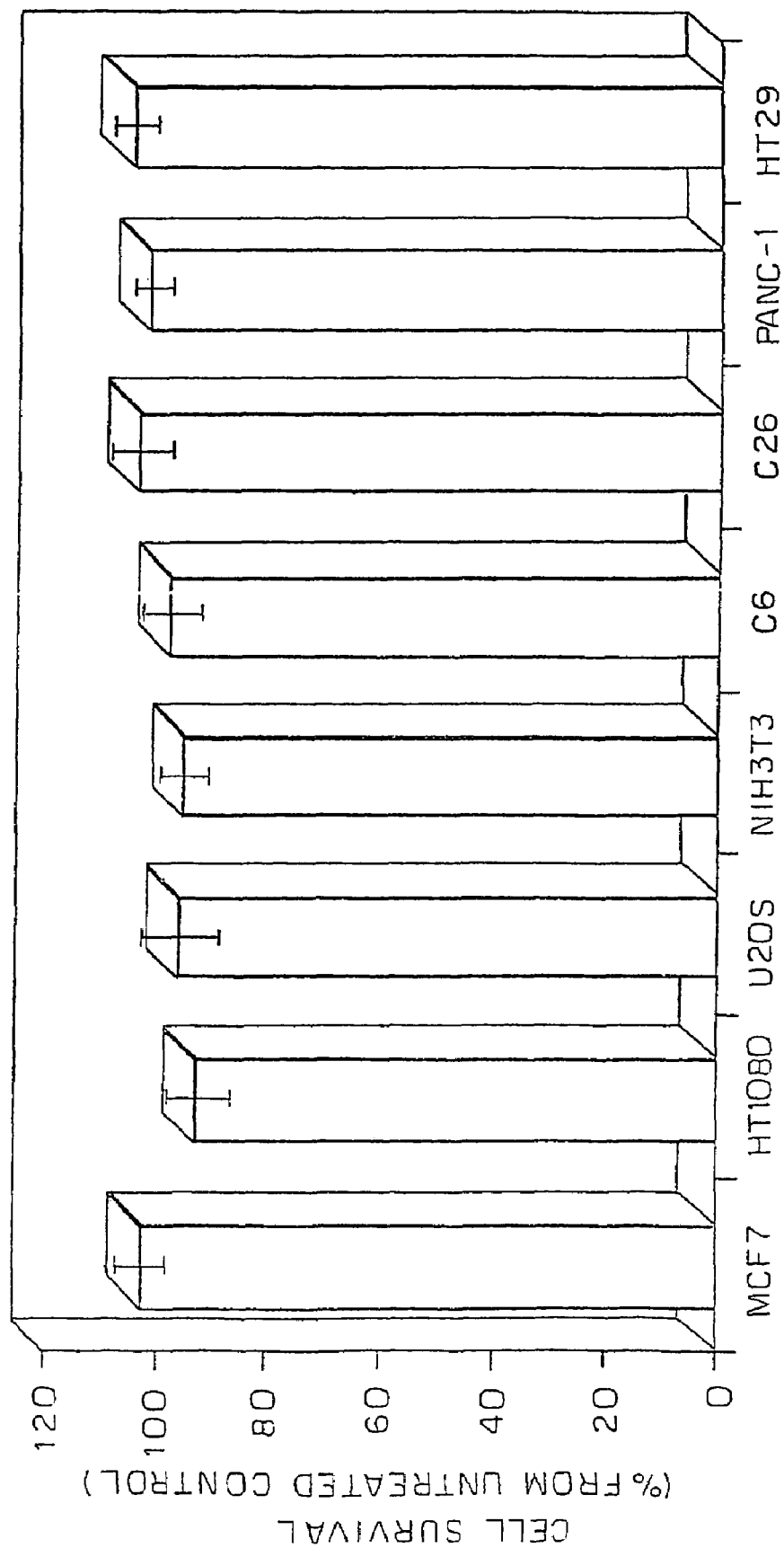
FIG. 10 depicts the results of toxicity testing of free drug delivery system (DDS) nanoparticles. DDS dose was 1 mg/ml and the incubation time was 24 hours. Each bar is an average of 32-64 independent determinations, and the error bars represent the standard deviations.

Toxicity testing of the free DDS was done as follows: cells of a given line were incubated with increasing concentrations of the DDS, spanning the range of 0.01-5 mg/ml, for 24 or 48 hours. Control cells were not exposed to the DDS. These tests were performed with 8 different cell lines, originating from human, rat and mice. The common feature of all eight cell lines was that they have receptors for hyaluronic acid. Results similar to those for the DDS dose of 1 mg/ml, as shown in FIG. 10, were over the whole DDS concentration range tested (i.e., 0.01-5 mg/ml). The data in FIG. 10 demonstrate that over all the DDS doses, incubation periods and cell lines this DDS is not toxic to cells.

Gene Transfection

The ability of the DDS to entrap plasmids at exceptionally high affinity, was reported in Tables 4 and 5. The potential of such a formulation to transfect cells with a desired plasmid that would result in expression of the encoded protein was tested in vitro.

The cell lines tested were PANC-1 and C6, both cell lines with receptors for hyaluronic acid. The reporter gene was the one encoding for Green Fluorescent Protein (GFP). The DDS was compared to two commercially-available vectors that served as "benchmarks": Polyplex—a cationic polymer, and lipofectamine—a cationic liposome. Protocols used for the commercial vectors were those recommended by the manufacturers.

The plasmid was entrapped in the DDS (microparticles), and was allowed to equilibrate for 24 hours prior to use. The DNA concentration was the same for all three vectors, 1.5 μg/well. Cells were incubated with the selected vector-DNA formulations in DMEM for 5 hours; control wells were incubated for the same period in DMEM alone. At the end of 5 hours, serum-supplemented cell growth media was added to all wells.

Cells were viewed under an inverted fluorescent microscope at 12 and at 24 hours from the starting point. The total number of cells, and the number of fluorescent cells in the viewed sample were counted. These data were used to calculate the transfection efficiency, defined as the % fluorescent cells of the total cells, in the viewed sample. The total number of cells in a viewed sample was 200-400 cells. Cell viability was tested upon termination of the experiment, 24 hours from the starting point.

The results obtained are listed in Table 8. The doses used for the benchmarks were 2 mg/ml (as recommended in their established protocols) and for the DDS 0.2 mg/ml was used, a ten fold lower dose. The DNA concentration was the same for all three. At 12 hours the gene product, GFP, was detected with the established vectors. This finding, although expected, was encouraging since the cell lines tested were those of special therapeutic interest, but not the classical cell lines (such as COS 7) used in transfection. With the DDS, 24 hours was required for protein expression. The transfection efficiencies for each of the three vectors, in both cell lines, also listed in the table, show that the performance of the DDS vector works as well as the bench marks, at a tenth of the dose (0.2 mg/ml vs. 2 mg/ml).

TABLE 8

In Vitro Gene Transfection

| Vector Species | mg/ml | Time to Detection (hours) | Transfection Efficiency at 24 Hours (%) | | Cell Viability (% from Untreated Control) |
|---|---|---|---|---|---|
| | | | PANC-1 | C6 | |
| Polyfect | 2 | 12 | 18 | 20 | <50 |
| Lipofectamine | 2 | 12 | 12 | 15 | <50 |
| DDS | 0.2 | 24 | 19 | 19 | 100 |

One of the severe drawbacks of gene transfection vectors that are cationic polymers or cationic lipids is toxicity. This was observed for the two established vectors here—in each cell line, the level of viable cells at 24 hours was less than 50% compared to the untreated control. In contrast, there was no toxicity with the DDS vector. Cell viability remained as high as that of the control cells. The toxicity data reported in the previous section suggests that the DDS doses elevated to those of the established vectors, 2 mg/ml, would also not have been toxic.

The data clearly support the potential application of the novel DDS in gene therapy. There appear to be two distinct advantages over competing non-viral vectors: (1) in two different cell lines it was as good as established vectors at a 10 fold lower concentration to achieve the same level of protein expression, suggesting that for equal vector concentrations the DDS system may be significantly superior to its competitors; and (2) in two different cell lines, no toxicity occurred with the DDS vector system, whereas the other two vectors used were quite toxic.

Treatment of MDR Tumors

In cell culture studies designed to evaluate the cytotoxicity of a drug-entrapping targeted carrier, compared to the same dose of free drug, the experimental design—and therefore the results—is usually biased in favor of the free drug. This is due to the static vs. dynamic conditions, for the in vitro and in vivo situations, respectively. In vitro, the free drug is in continuous contact with the cells for the duration of the experiment, usually 24 hours or more. In vivo duration of drug—administered in free form—at the tumor site will be much shorter, due to the limited time span of administration and the natural clearance processes. In vitro performance of a drug/carrier formulation (even a targeted carrier) may not be much different than that of the free drug, under incubation periods of 24 hours or more. In contrast, in vivo—if the carrier adheres to the target and stays there as a sustained release depot, drug supply to the tumor site may be much higher (dose and duration) than the free drug, resulting in enhanced cytotoxicity.

In order to reduce the in vitro bias in favor of free drug, cells were exposed to the following treatment formulations: free drug, drug entrapped in the DDS, and free DDS for a period of only 4 hours. The treatment media was then replaced with serum-supplemented cell growth media free of any drug or carrier, and the number of viable cells was determined 20 hours later (24 hours from start). If some of the carrier formulation adhered to the cells, it should remain there as a depot despite replacement of the media, and continuously feed the cells with drug while the cells that received free drug would not be exposed to any more drug, once the media was replaced.

Figure 11A:
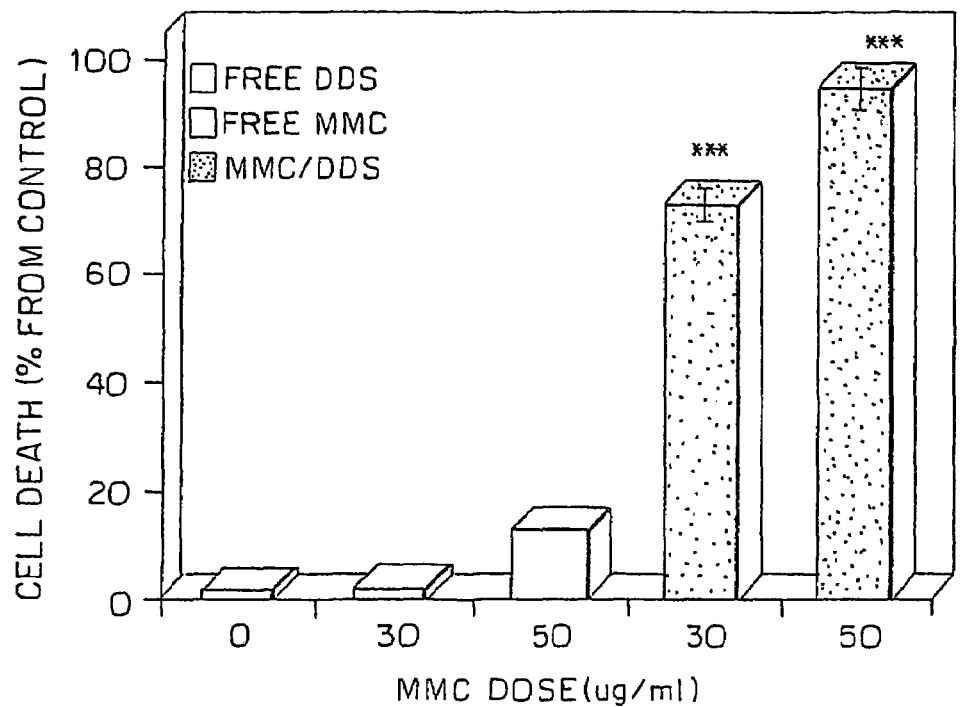
FIGS. 11A and 11B show the cytotoxic effects of MMC (FIG. 11A) and of DOX (FIG. 11B), formulated in the DDS. (nano particles) in C26 cells exposed to the treatment media for 4 hours, compared to free drug and free drug delivery system (DDS). *** indicates p<0.001, comparing for each drug species and dose the carrier vs. free formulations.
Figure 11B:
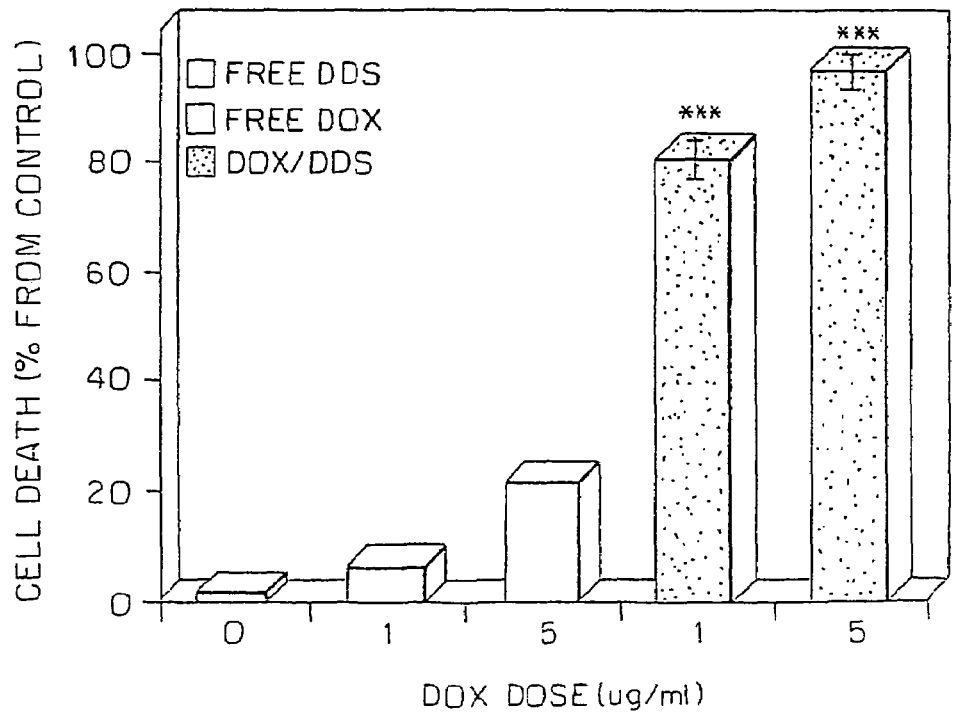

Typical results showing the increase in cell death (compared to untreated control) as a function of treatment formulation, are shown in FIG. 11, for the cell line C26. This is an inherent multidrug resistant (MDR) line originating from mouse colon carcinoma. In FIG. 11A the results with the drug mitomycin C (MMC) are shown. As expected from the previous in vitro toxicity studies (FIG. 2), free DDS (tested here with the dose of 1 mg/ml) was not toxic. Two doses of free MMC 30 and 50 µg/ml were hardly effective, resulting in cell death percentages of under 15%. This low response to rather high doses is a manifestation of the MDR nature of these cells. In contrast, when treatment was with the same drug doses but entrapped in the DDS, 80-100% of the cells were killed. The differences in response for each drug dose—carrier-mediated vs. free—are highly significant ($p<0.001$). Similar results are shown in FIG. 11B for another drug, doxorubicin (DOX). Free drug (each drug species has a different dose range) is ineffective while the same doses formulated in the carrier were highly effective, also generating 80-100% cell kill. Comparable results were obtained with two other cell lines—C6 and PANC-1. All three line tested have HA receptors.

EXAMPLE 9

In Vivo Studies

In Vivo Studies I: Tumor Chemotherapy

Female BALB/c mice which were 8 weeks old at initiation of the experiment were used. The tumor model employed was C-26 cells (originating from mouse colon carcinoma) injected subcutaneously into the right hind footpad. The chemotherapeutic drug was mitomycin C (MMC) free, or entrapped in DDS, LLG, in nanoparticulate form. The MMC dose was 2 mg/kg body, in both free and DDS formulations and the DDS dose was 1 mg/ml.

Experimental Design for Run 1

The experiment was performed with 20 animals, divided into 4 groups, each group of 5 mice receiving a specific treatment as listed in Table 9, below.

TABLE 9

Animal Groups

| Group # | Treatment |
| --- | --- |
| 1 | Saline |
| 2 | Free DDS |
| 3 | Free MMC |
| 4 | MMC/DDS |

To provide the tumor, C-26 cells were grown in cell culture flasks. At day zero, the cells were harvested, washed several times, counted and immediately injected. The injected dose was $8\times10^5$ cells in 30 µl.

Treatments were given on days 5, 12 and 19. Administration was by injection into the tail vein. All injected volumes were 0.1 ml.

Experimental Design for Run 2

Experimental design was essentially similar to that of Run 1, with the following changes:
  a. Drug dose was elevated to 5 mg/ml.
  b. Tumor inoculation dose was $8\times10^5$ cells in 30 µl.
  c. The experiment was conducted with 2 groups, one receiving free DDS and the other MMC/DDS, with 3 and 5 mice per group, respectively.
  d. Treatment were given on days 14, 17, 20 and 23.
  e. Tumor size at initiation of treatment was 75 mm$^3$.

Parameters measured for Run 1 were retention in circulation, tumor onset, tumor volume, survival. Parameters measured for Run 2 were survival.

Results for Run 1: Retention in Circulation

The reticuloendothelial system (RES) as part of its normal physiological processes, operates to remove foreign particulate matter from the circulation rather swiftly. Unless the target of an intravenously (i.v.) administered particulate carrier is within the RES, this removal is a major problem for all i.v.-administered particulate carriers, since the it reduces the likelihood of a sufficient dose reaching its intended target in an efficacious manner. This problem is not specific to tumor treatment. It is general for any pathological situation that requires i.v. administration.

Through extensive studies, means to block this process, thus allowing for long-term circulation of particulate matter, sum up to the following combination: the particle should be small and it should have a hydrophilic coat, usually due to an abundance of hydroxyl residues. Particulate carriers of the sphere type—made on the nano scale (nanospheres)—are usually coated by polymers such as poloxomar or poloxamine. Small liposomes usually carry polyethylene glycol (PEG) on their surface, and come under names such as "stealth liposomes", "PEGylated liposomes" and "sterically-stabilized liposomes".

Upon commencing the invention and development of the present DDS, it was hypothesized that due to hyaluronic acid being its major component the surface of the particle will be rich in hydroxyl residues that will provide it with an intrinsic ability of long retention in circulation and with targeting ability. These would be distinct advantages over the competitive carriers, as both targeting and "stealth" properties are already built in.

Figure 12:
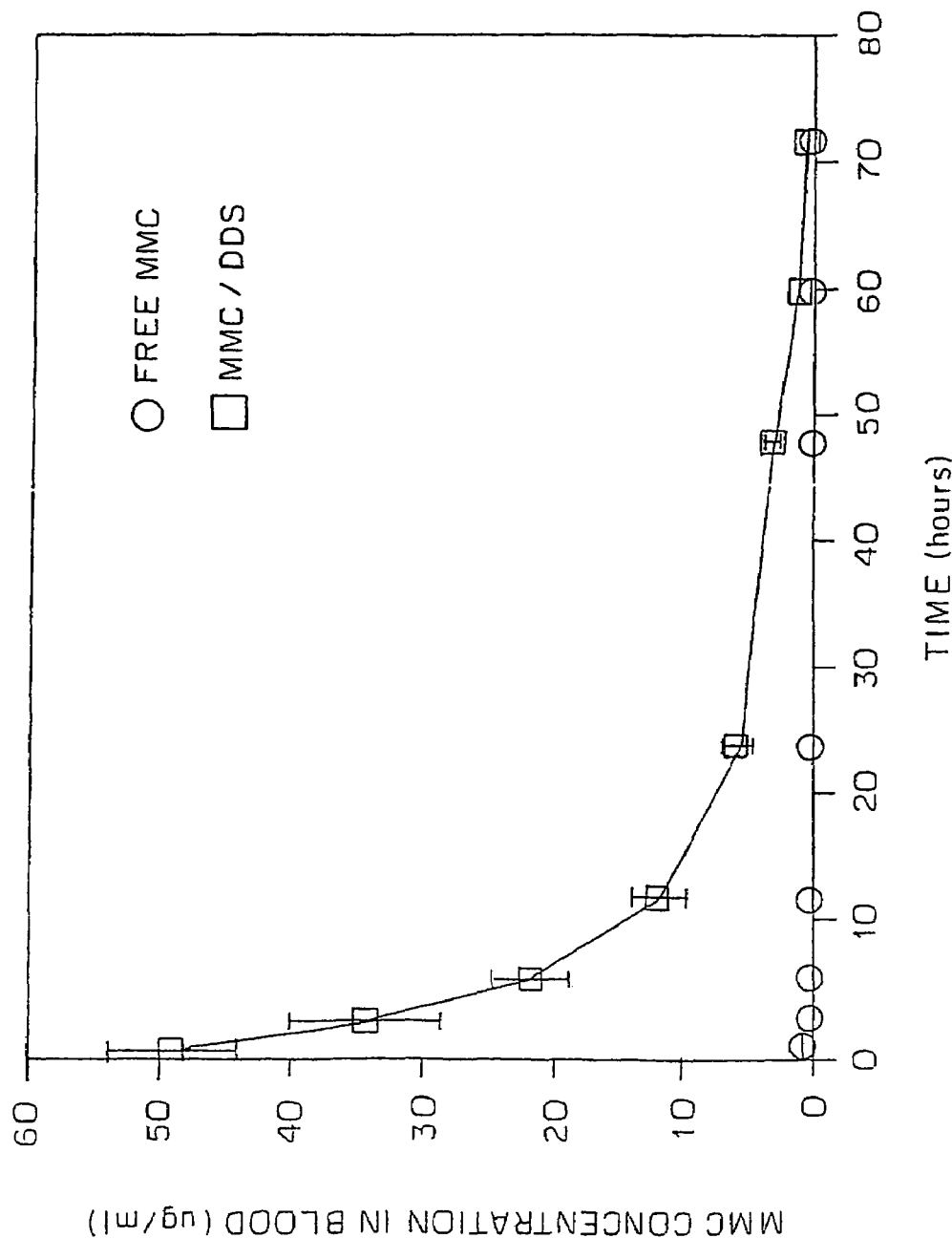
FIG. 12 depicts the concentrations of MMC in blood, as a function of formulation type and time from injection. Each symbol is an average of 5 animals and the error bars represent the standard error of the mean (SEM). The lines are non-theoretical, drawn to emphasize the trends of the data.

At selected periods post-injection, animals receiving drug-containing formulations were bled, and samples were treated according to established protocols. MMC concentration was determined by HPLC assay. Typical results of the retention in circulation, comparing free MMC to MMC entrapped in the carrier (MMC/DDS) are shown in FIG. 12. The data show that free MMC disappears very quickly from the circulation, whereas MMC administered in the carrier circulates for a much longer period of long time. This finding was reproduced from one injection to another, and drug was found in the circulation when administered via the carrier up to 72 hours post-injection. The fast disappearance of free drug indicates that the MMC found in the circulation of the animals receiving the MMC/DDS formulation is in the carrier. These results confirm the hypothesis, discussed above, that these DDS have intrinsic "stealth" capability. As indicated above, this carries positive implications beyond the specific pathology tested here.

Results for Run 1: Tumor Onset and Tumor Volume

Figure 13:
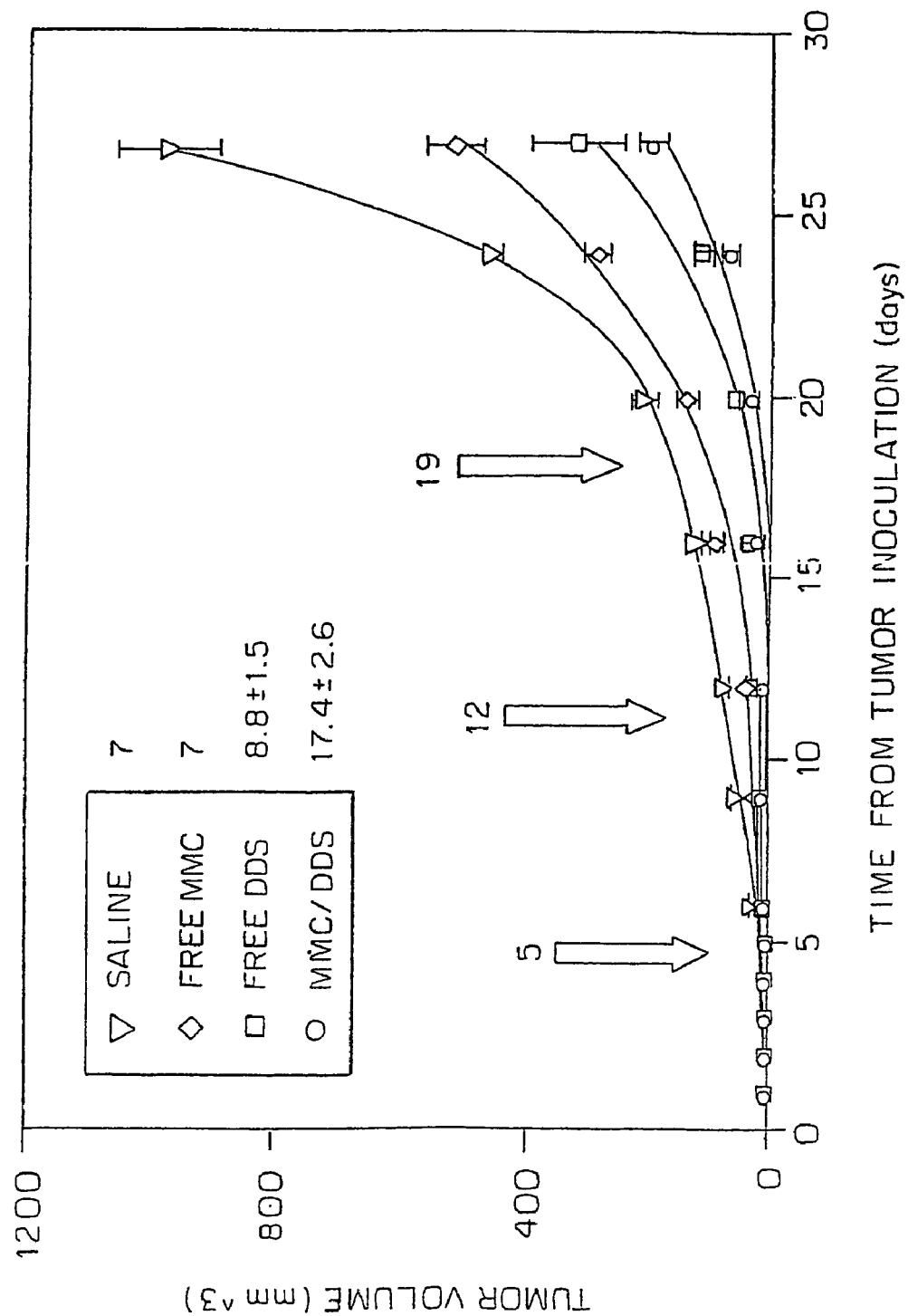
FIG. 13 illustrates the increase in tumor volume with time. Points are experimental, each an average of 5 animals; the error bars are the SEM and the curves are non-theoretical, indicating the trends in the data. The arrows and the numbers above them indicate treatment days. The numbers next to the symbols are days of tumor appearance.

Results of the increase in tumor volume, for all 4 groups, are shown in FIG. 13, together with the average day on which tumors were first detected. In all animals receiving saline alone, tumor was detected on day 7, and it increased fast and exponentially. Tumor was detected on day 7 in all animals receiving free drug as well. The increase in tumor volume, despite receiving 3 doses of a chemotherapeutic drug, was not much different than in the saline group. This indicates that the MDR nature of this cell line previously seen in vitro (FIG. 3) also persists in vivo. Surprisingly, treatment with free DDS was better than saline and than free drug. Average day of tumor appearance was 9 (vs. 7), and the tumor growth rate was distinctly slower. Tumors were also significantly smaller compared to the saline and free drug groups.

The performance of the free DDS in vivo is quite different from that observed in vitro. Hyaluronic acid is one of the key components of extracellular matrix (ECM) and it is known that tumor cells that have receptors for HA make use of this. Through interaction of their HA receptors with the HA in the ECM, the tumor cells may use the ECM as a platform in the course of tumor progression. Blocking the receptors may, therefore, delay tumor progression. This could be a major mechanism responsible for the results obtained with free DDS, where the carrier binds to HA receptors and is able to block them. Other potential mechanisms, not mutually exclusive, are performance of the free DDS as an anti-angiogenic factor or as a general boost to host-defense mechanisms. The mechanisms responsible for this positive effect of the DDS itself will be pursued in order to understand these phenomena and learn how to exploit them for better therapeutic outcomes. Regardless of its origins, this is a positive additional advantage of this DDS, which was not anticipated on the basis of the in vitro data.

The best results were obtained with the drug entrapped in the carrier. As seen in FIG. 13, tumor was first detected on about day 17, much later than in the groups treated with free DDS, free drug, or saline. Tumor growth rate was slowest and tumors were smallest, of all groups tested. Perhaps this is due to the intrinsic targeting of this DDS wherein the fraction that reached the tumor remained there, acting as a drug depot and possibly combining the cytotoxicity effect of drug and the carrier effect seen with free DDS. The in vitro results that showed that this formulation, unlike free drug, was capable of killing MDR cells, were thus repeated and confirmed in the in vivo case also.

Results for Run 1: Survival

Figure 14:
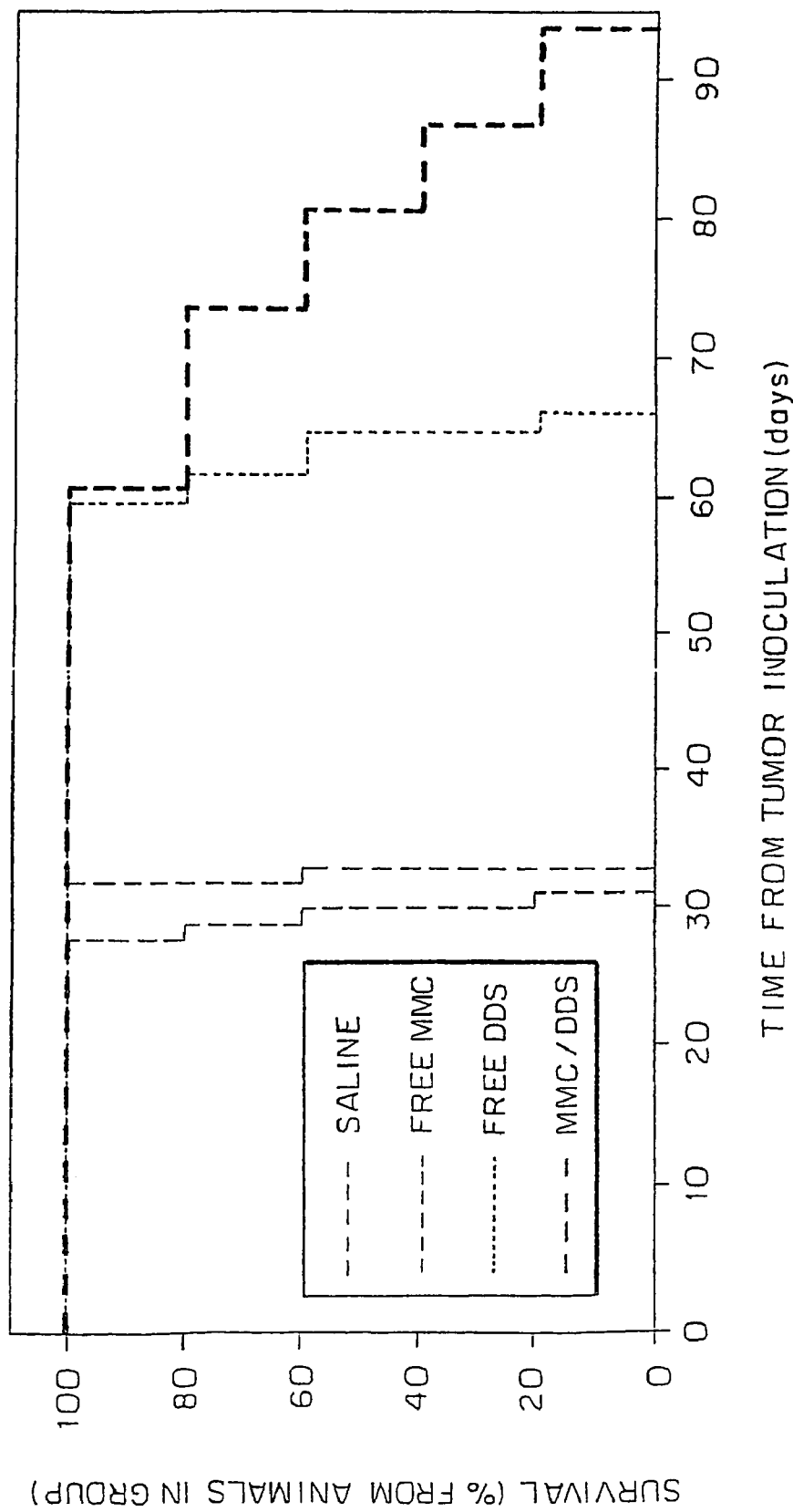
FIG. 14 illustrates the survival of the animals in Run 1. Each animal received 3 injections of the selected formulation. Data for the saline and free MC groups are from 10 animals/group; data for the free DDS and the MMS/DDS are from 5 animals/group.

Animal survival was monitored for over 90 days until the last animal died. The results are shown in FIG. 14.

All animals from the groups receiving saline died between days 29 and 31, and those receiving free drug died between days 31 and 33. The animals receiving the free DDS survived twice as long as the saline and free drug groups, dying between days 59 and 66.

This long survival carries two critical implications. The first is that this DDS has no in vivo toxicity as was previously shown in vitro. The weight of the in vivo evidence is much more significant in its implications for all applications of this technology. The second implication is that, concurrent with the effect on tumor development and size (FIG. 13), the free carrier by itself has a beneficial therapeutic effect on tumor bearing animals.

The longest survival, 3 times as long as for the saline and free drug groups, was observed for the animals receiving the full treatment, the drug entrapped in the DDS. The last animal died on day 94. This is exceptionally long survival for tumor-bearing mice, especially in an MDR case, and indicates the superiority of this drug delivery technology compared to its competitors.

Results for Run 2: Survival

Figure 15:
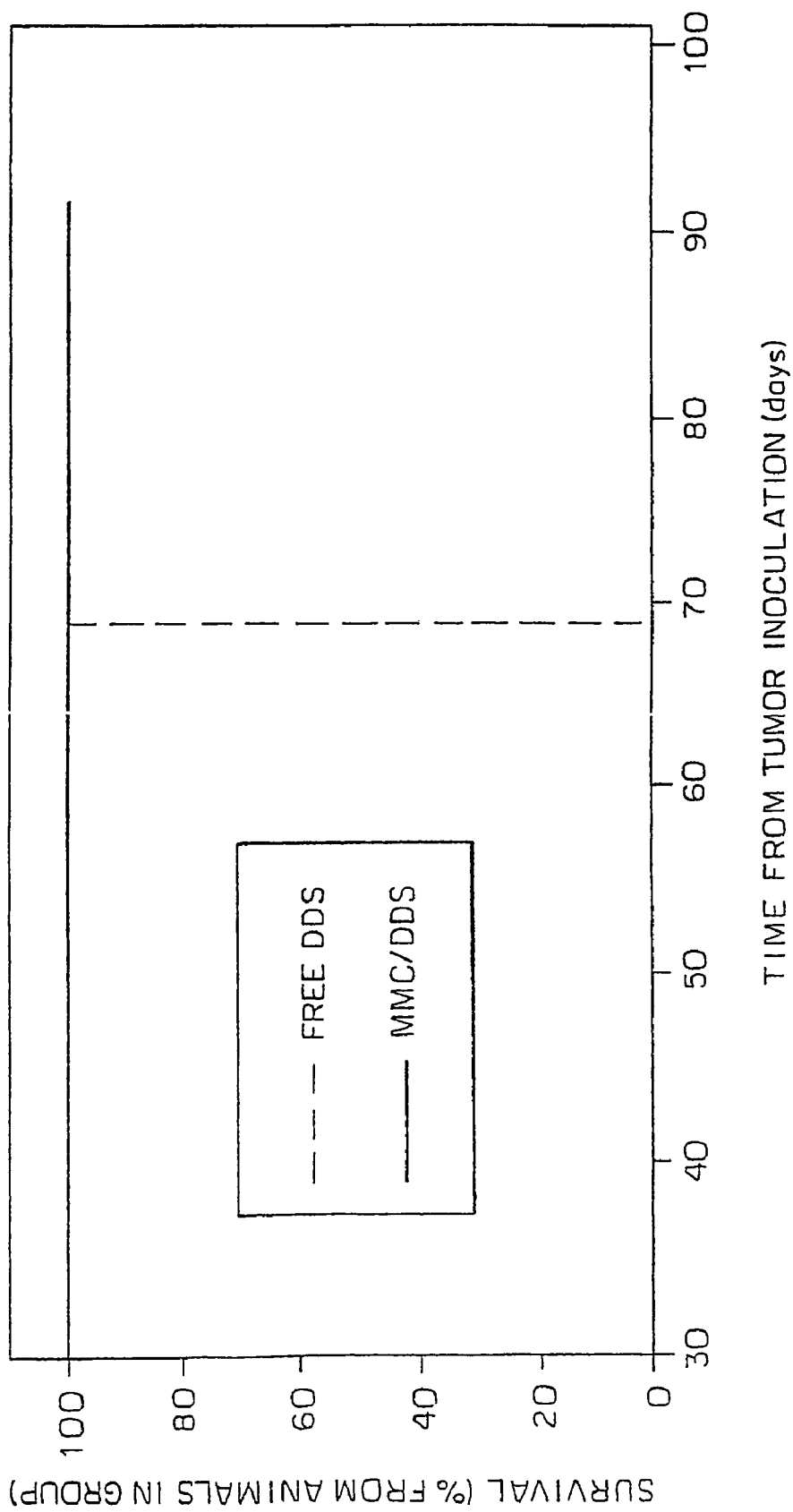
FIG. 15 illustrates the survival of animals in Run 2. Each animal received 4 injections of the selected formulation. Data for the free DDS is from 3 animals and for the MMC/DDS from 5 animals.

Animal survival was still being monitored on day 91 of the experiment, and the results are shown in FIG. 15. The three tumor-bearing animals treated with the free DDS were the longest survivors, up to 69 days. The five tumor-bearing animals treated with the MMC/DDS formulation fared even better, as at 91 days post tumor inoculation all animals were alive.

The trend of these data is similar to that obtained in Run 1, showing that the exceptional responses to the novel DDS are reproducible. Two major differences existed between the two experiments. First, in Run 2 the treatment was initiated after the tumor was developed (see experimental design above), which makes it a more challenging therapeutic situation compared to Run 1. Secondly, in Run 2 the animals received a higher cumulative drug dose. There were 4 injections (vs. 3 in Run 1) and the dose was 2.5 fold higher (5 vs. 2 mg/ml).

The positive trend these differences induced indicates a potential to generate even better responses with the novel DDS. More challenging but also more realistic models, in which the tumor grows up to the size range of 100-150 $mm^3$, before treatment is initiated may be amenable to the novel DDS approach.

EXAMPLE 10

In Vivo Studies II: Intranasal Delivery to the Brain

Treatment of neurodegenerative diseases requires drug delivery to the brain, either crossing an intact BBB or bypassing it. Two experiments, one in rats and the other in mice, were conducted to evaluate the ability of the novel DDS of the present invention to deliver drugs to the brain, bypassing the BBB via intranasal (IN) administration.

Run 1 comprised a rat experiment. Healthy pigmented rats were used. The DDS was LLG, in nanoparticulate form and the marker was MMC. The test system was the marker formulated in the novel DDS. The dose administered was 5 mg/kg body, in both free and DDS formulations, 300 μl/animal. The DDS dose was 1 mg/ml.

The experiment was conducted with 4 animals, divided into two pairs. One pair received the free marker, intranasally (IN), into the right nostril. The other pair received the marker/DDS formulation, IN, into the right nostril. Administration was slow, over several minutes, using an appropriate needleless syringe.

At 6 hours post administration, the animals were sacrificed and the brains were removed. Each brain was soaked in 10 ml PBS for an hour, to desorb loosely attached marker, after which the brains were homogenized. The marker was assayed in the wash and in the brain homogenates, using an HPLC assay.

Figure 16:
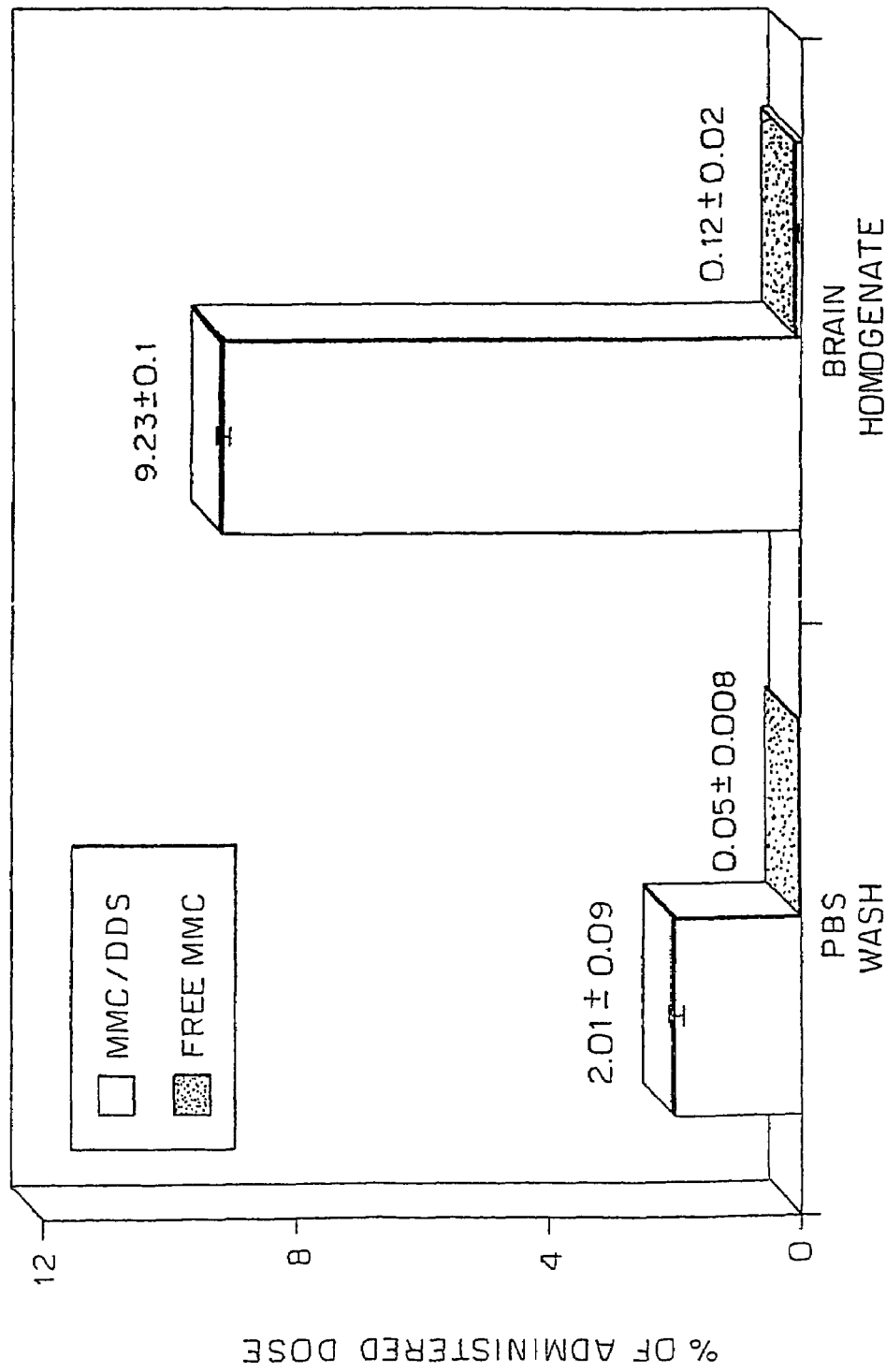
FIG. 16 is a bar graph showing the brain accumulation of MMC, used as a marker, following intranasal (IN) administration of free MMC and MC entrapped in DDS nanoparticles. Data is from Run 1, an experiment with rats.

The results obtained are shown in FIG. 16, wherein the marker accumulation is presented as % from administered dose. Even though there were only 2 animals per treatment group, the agreement within each group was good enough to allow averaging. The average and standard deviation for each pair, in the wash and in the brain homogenate, are listed above the relevant bars.

Focusing on the brain homogenate, marker accumulation in the brain when administered in free form was negligible, on the order usually seen with free small molecules, as was expected. In contrast, when administered in the DDS form, there was substantial accumulation of the marker in the brain—close to 10% of administered dose. This is a high value by itself (80 fold higher than free drug), especially if this can also be achieved with drugs of interest. These results indicate the high potential this novel DDS has for pathological conditions that require drug delivery to the brain.

Run 2 comprised a mouse experiment. The animals used were healthy C57BL/6 mice. The DDS was LLG in nanoparticulate form. The marker was MMC; the test system was the marker formulated in the novel DDS. The dose administered was 5 mg/kg body weight, in both free and DDS formulations, 150 μl/animal. The DDS dose was 1 mg/ml.

The experiment was conducted with 4 animals, divided into two pairs. One pair received the free marker, IN, into the right nostril. The other pair received the marker/DDS formulation, IN, into the right nostril. Administration was slow, over several minutes, using an appropriate syringe.

At 6 hours post administration, the animals were perfused through the heart, after which they were sacrificed. The brains were removed, homogenized, and the marker concentration was determined, as in Run 1.

Figure 17:
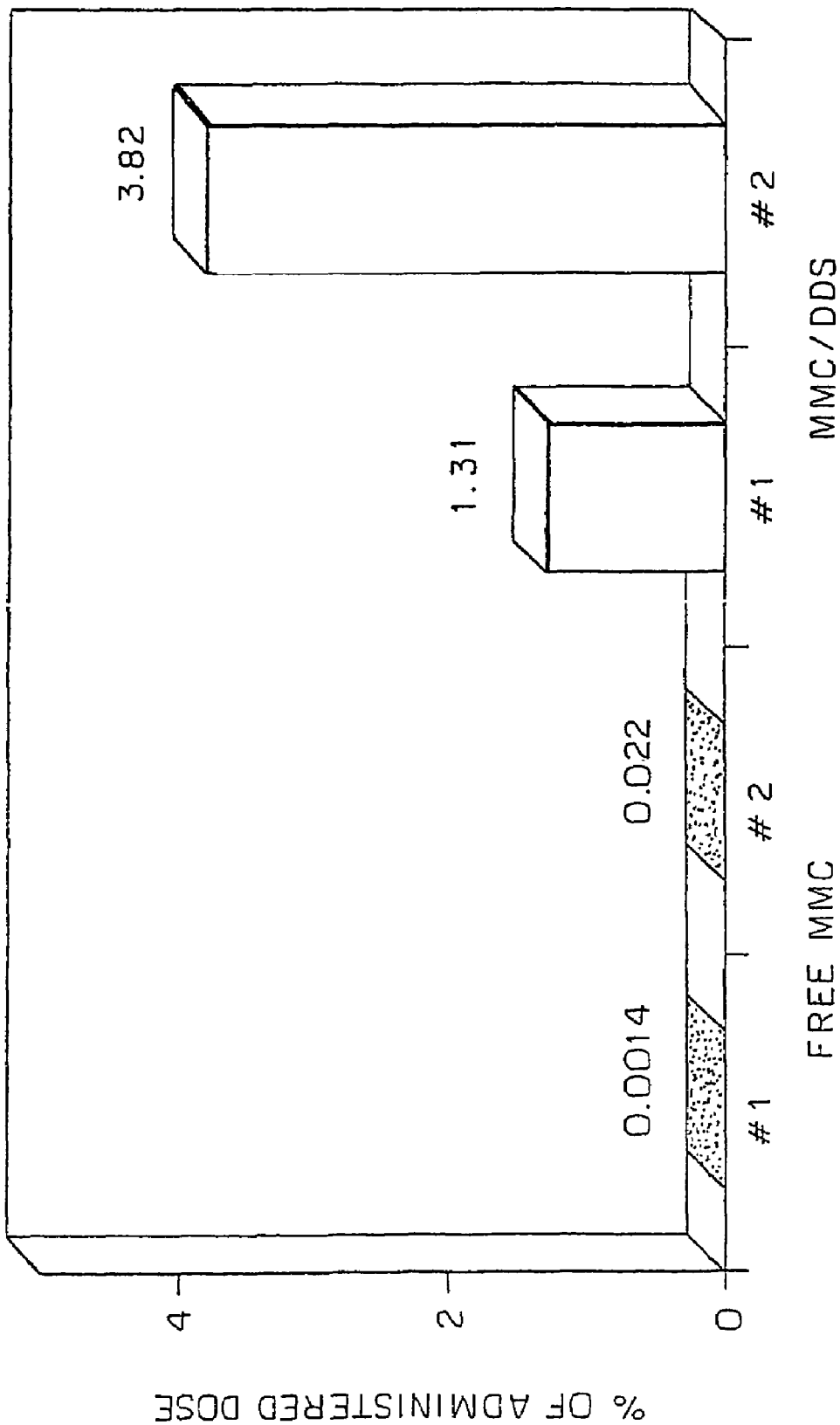
FIG. 17 is a bar graph showing the brain accumulation of MMC, used as a marker, following intranasal (IN) administration of free MMC and MMC entrapped in DDS nanoparticles. Data is from Run 2, an experiment with mice.

The brains, post perfusion, were clean. The results obtained, expressed as % of administered dose, are shown in FIG. 17. The data are reported per animal due to the animal-to-animal variability. Despite the variability, the results are quite clear: negligible accumulation of marker occurred when it was administered in free form, and significant accumulation when administered in the DDS form. As in the case of rats, the accumulation found when the marker was administered in the carrier constitutes a positive finding in and of itself, and is 600-2,500 fold higher than when the marker was administered in free form. These results show that the potential of this drug delivery technology to deliver drugs to the brain in a non-invasive route of administration is not limited to a single animal species.

EXAMPLE 11

Animal Study Testing the Novel DDS in the Treatment of Drug-Resistant Tumors in Mice: A Tumor Metastasis Model The objective in the present study was to evaluate the novel DDS in a tumor metastasis model. Similar to the previous study using mice and the inherent-MDR C-26 cell line, this study also involves an inherent MDR cell line, B16F10, from mouse melanoma. The specific protocol implemented is established in the field and is designed to induce metastasis in the lungs.

C57BL/6 female mice were used, which were 12 weeks old at initiation of the experiment. The tumor model was B16F10, cells injected i.v. The chemotherapeutic drug employed was mitomycin C (MMC). The DDS system was LLG in the form of nano particles. The test system was MMC formulated in the novel DDS of the present invention, denoted MMC/DDS. The dose of MMC injected was 5 mg/Kg of body weight and the DDS dose was 1 mg/ml.

The experiment was performed with 25 animals, divided into 5 groups, each group of 5 mice receiving a specific treatment as listed in Table 10. Group 1 is a control group of healthy mice that were not inoculated with tumor cells.

TABLE 10

| | Animal Groups | | | |
|---|---|---|---|---|
| | | Group # | | |
| 1 | 2 | 3 | 4 | 5 |
| Treatment None | Saline | Free MMC | Free DDS | MMC/DDS |

B16F10 cells were grown in cell culture flasks. At day zero, the cells were harvested, washed several times, counted and immediately injected to groups 2 to 5. The injected dose was $5 \times 10^5$ cells in 50 μl PBS.

Treatments were given on days 1, 5 and 9. Administration was by injection into the tail vein. All injected volumes were 0.1 ml. The experiment was terminated 21 days post tumor inoculation. The animals were sacrificed, and the lungs were removed, weighed, and fixed in Bouin's solution. Lung weight increase was calculated using the following formula:

Lung weight increase (%)=100×(tumor lung weight−normal lung weight)/normal lung weight Surface metastases were counted by an expert using a dissecting microscope. Sample codes were blinded so that the expert did not know the treatment each source animal received.

Quantitative evaluation of metastases in the lungs can be performed by two independent measurements: actual counting of the metastases in excised and properly fixed lungs; and/or measurement of the increase in the weight of the lungs due to the metastases in the animals injected with tumor cells. Both techniques were implemented in the present study.

Figure 18:
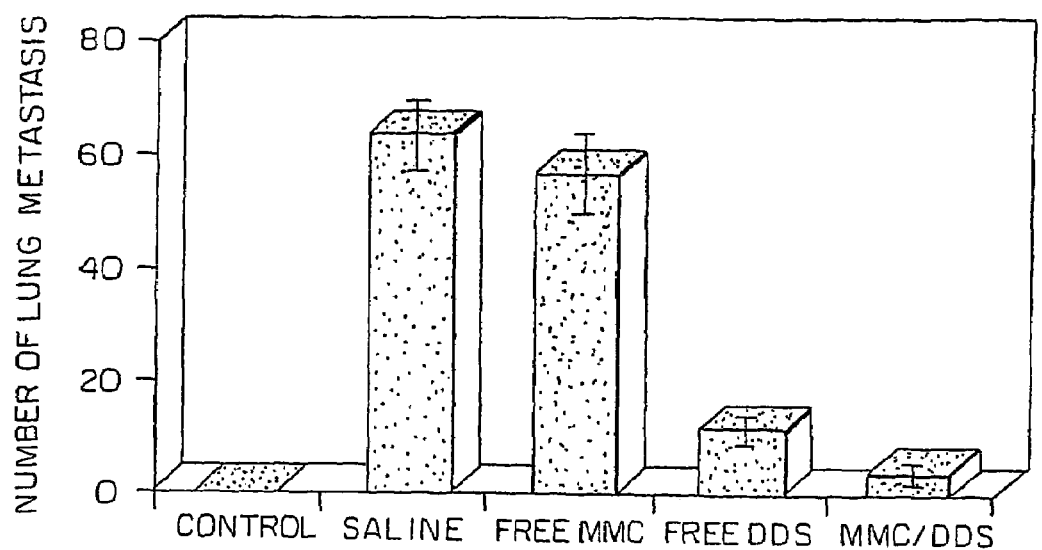
FIG. 18 shows the number of metastases found in the lungs of the C57BL/6 mice injected i.v. with B16F10 cells. The control group represents healthy animals that were not injected with tumor cells. Each bar is an average of the five animals in the group and the error bar is standard deviation.

The number of metastasis found in groups 1 to 5 are shown in FIG. 18.

As expected, there were no metastases in the lungs of the control animals that did not receive any tumor cells. All other groups that received the i.v. injected B16F10 cells developed lung metastases. The most aggressive metastatic situation developed in the animals that received saline or free drug. As can be seen, there is no statistical difference between these groups, indicating that the inherent MDR nature of these cells is expressed in vivo also.

Treatment with the free DDS is seen to generate a 6 fold decrease in the number of metastases compared Lo saline, and treatment with the test formulation generated a much higher reduction, on the order of 17 fold.

Figure 19:
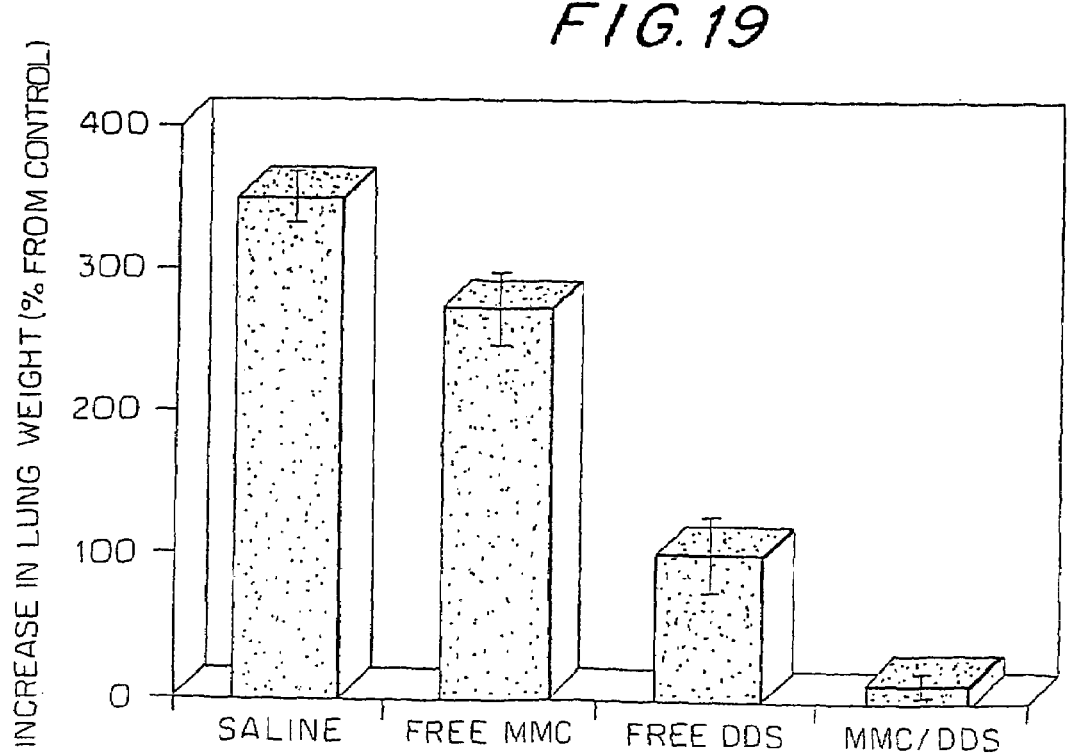
FIG. 19 shows the increase in lung weight of tumor-injected mice calculated from the raw data of lungs' weight, according to the formula listed in the experimental section. Each bar is an average for the 5 animals in the group and the error bars are the standard deviation.

In all four tumor-injected groups the weight of the lungs increased compared to that of normal animals (the control group). The results obtained are shown in FIG. 19.

The highest increase in lung weight—close to 400%—was seen in the animals that did not receive any treatment (the saline group), and the group receiving treatment with free drug was almost the same. The increase in lung weight was smaller than no treatment and free drug for the animals receiving the free DDS, but there was still a two-fold increase in lung weight compared to control group of healthy animals. The best response—both in relative (compared to the other groups) and in absolute (compared to healthy animals)

terms—was observed with the test formulation of the MMC entrapped in the DDS. The % increase compared to healthy animals was on the order of 10%, which is not statistically significant, indicating the potential of this formulation to abolish lung metastasis.

Figure 20:
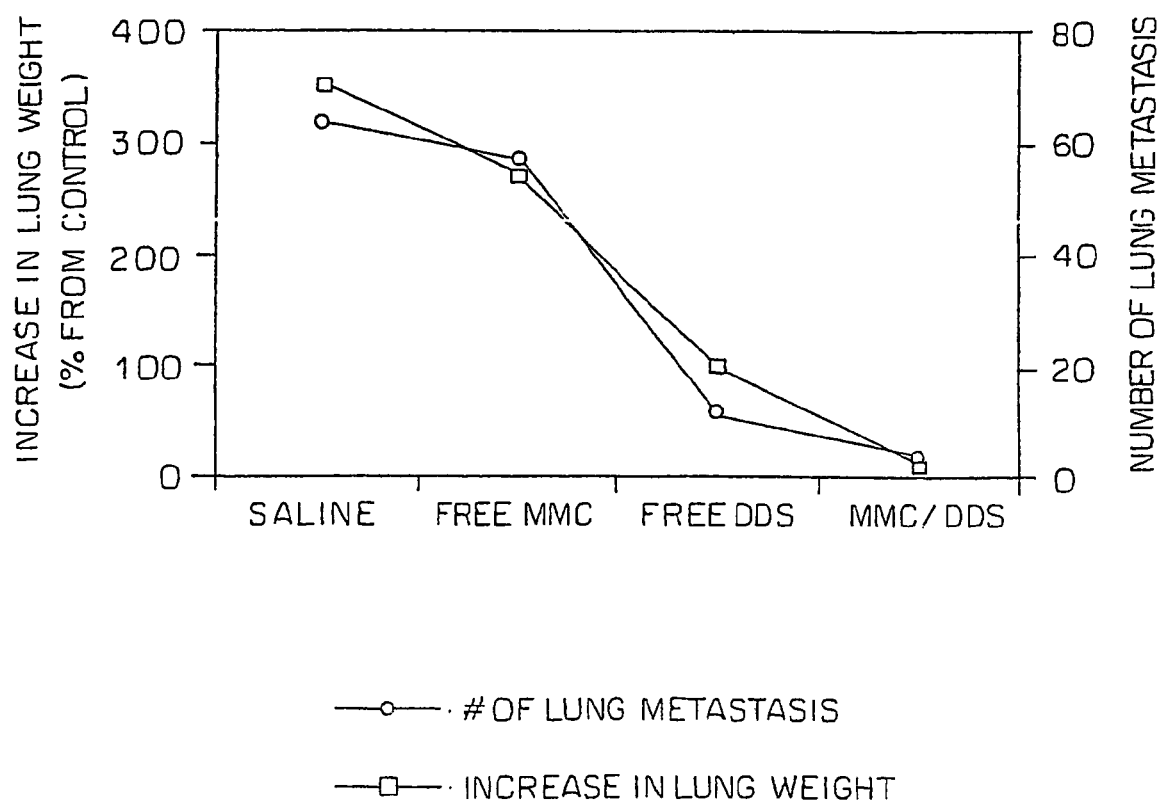
FIG. 20 represents a replotting of the data of FIGS. 18 and 19 (averages only). The points are the experimental data, and the solid lines are non-theoretical, drawn to emphasize the trends.

Because the lung metastases are responsible for the increase in lung weight, there should be a reasonable correlation between the two independently measured parameters. This was the case, as clearly seen in FIG. 20, where the data (averages only) of FIGS. 18 and 19 were replotted together. FIG. 20 also demonstrates the clearly superior performance of the test formulation in one of the most challenging tasks of tumor treatment, which is abolishing metastases from an MDR tumor.

To date, the performance of the novel DDS as a carrier for chemotherapeutic drugs in two independent animal models has been studied. One is a solid tumor and the other is lung metastases. In both models, tumor cells injected into the animals, from the C-26 and B16F10 cell lines were found to manifest in vivo their MDR nature previously seen in vitro.

In both models, treatment with the free DDS itself shows a better clinical response than free drug. However, in both models the best clinical response is seen with the test formulation of the novel DDS entrapping a chemotherapeutic drug. This indicates the high potential for this novel system in clinical use.

EXAMPLE 12

BSA-FITC Entry into MCF-7 Cells

Bovine serum albumin tagged with the fluorescent marker FITC (BSA-FITC) in both free form and entrapped in the DDS was used to determine whether DDS can also induce the entry of large macromolecules into cells. The free and the DDS-entrapped BSA-FITC were incubated at 25° C. for 60 minutes with confluent monolayers of MCF7 cells (originating from human breast carcinoma). MCF-7 cells are reported to have two known receptors for hyaluronic acid—ICAM-1 and CD44. The protein/DDS systems were cleaned from the free protein. The free and the entrapped protein were at the same concentration: 3.3 mg/ml. At the end of the incubation the cells were viewed by means of confocal microscopy.

Figure 21:
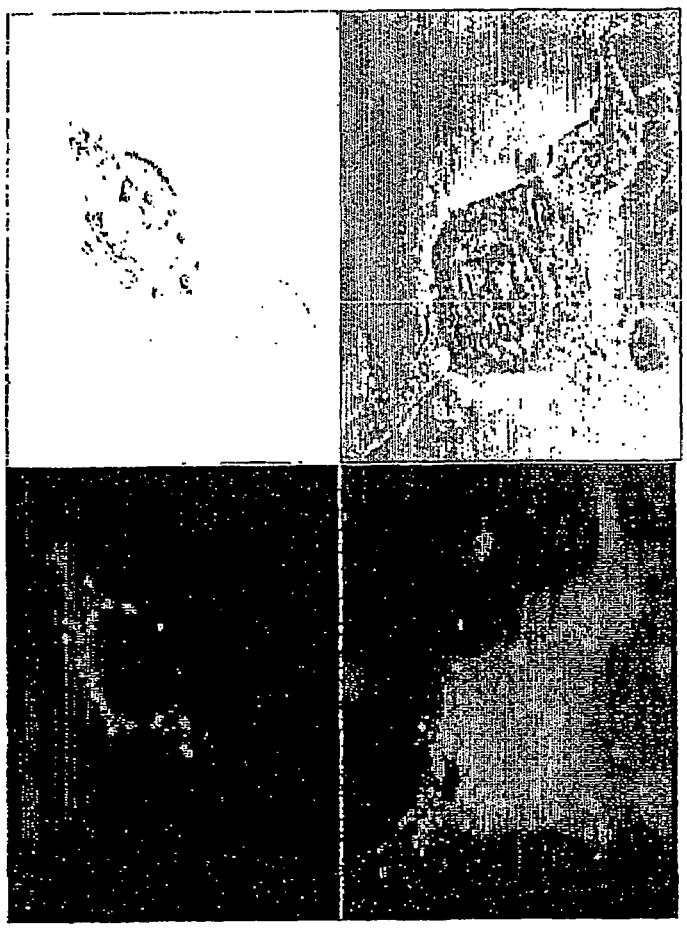
FIG. 21 depicts uptake of BSA-FITC entrapped gagomers into MCF7 cells using light and fluorescent microscopy. The upper two panels show uptake of free protein and non-specific binding. The lower two panels depict protein entry into the cytosol and nucleus.

The results shown in the upper two panels of FIG. 21, are for free protein. Some of the protein gained entry into the cell, and can even be seen bound to the nuclear envelope, but not inside the nucleus. BSA is known to bind non-specifically to cells, and may have gained entry through non-specific receptors or through pinocytosis.

The results in the lower two panels of FIG. 21 are for the DDS-entrapped BSA-FITC. Protein entry into the cells is considerably higher than for the free protein, and the protein has also gained entry into the nucleus. As in the case of the entrapped EtEr (FIGS. 2-4), the exact mechanism by which this occurred is not yet fully understood. The likelihood that the protein-DDS is taken up by receptor-mediated endocytosis is, however, even higher for the large protein than for the small EtBr.

The foregoing description of the specific embodiments will so fully reveal the general nature of the invention that others can, by applying current knowledge, readily modify and/or adapt for various applications such specific embodiments without departing from the generic concept, and, therefore, such adoptions and modifications should and are intended to be comprehended within the meaning and range of equivalents of the disclosed embodiments. It is to be understood that the phraseology or terminology employed herein is for the purpose of description and not of limitation.

REFERENCES

Balazs et al, "Cross-linked gels of hyaluronic acid and products containing such gels", U.S. Pat. No. 4,582,865, issued Apr. 15, 1986
Bangham AD, "Liposomes: the Babraham connection", *Chem Phys Lipids* 64(1-3):275-285 (1993)
Benita. et. al, "Submicron emulsions as colloidal drug carriers for intravenous administration: comprehensive physicochemical characterization", *J Pharm Sci* 82(11):1069-1079 (1993)
Gottesman et al, "Genetic analysis of the multidrug transporter", *Annu Rev Genet* 29:607-649 (1995)
Gref et al., "Biodegradable. long-circulating polymeric nanospheres", *Science* 263(5153):1600-1603 (1994)
Larsen et al, "Resistance mechanisms associated with altered intracellular distribution of anticancer agents", *Pharmacol Ther* 85 (3):217-29 (2000)
Margalit et al, *J Controlled Release* 17:285-296 (1991)
Nutt et al, "Differential expression of drug resistance genes and chemosensitivity in glial cell lineages correlate with differential response of oligodendrogliomas and astrocytomas to chemotherapy", *Cancer Res* 60(17):4812-4818 (2000)
Van den Hoogen et al, "A microtiter plate assay for the determination of uronic acids", *Anal Biochem* 257(2):107-111 (1998)
Wolff et al, "Chemosensitivity of glioma cells in vitro: a meta analysis", *J Cancer Res Clin Oncol* 125(8-9):481-486 (1999)
Wu et al, "In vivo versus in vitro degradation of controlled release polymers for intracranial surgical therapy" *J Biomed Mater Res* 28(3):387-395 (1994)

What is claimed is:

1. A water-insoluble lipidated glycosaminoglycan particle in the form of a sphere with the glycosaminoglycan portion of the particle forming a shell on the outside and the lipid portion of the particle forming the inside, without the presence of liposome, said particle comprising the reaction product of at least one glycosaminoglycan having a molecular weight within the range of about $1 \times 10^5$ to about $1 \times 10^7$ daltons, with a lipid consisting of a phosphatidylethanolamine, wherein the ratio of said phosphatidylethanolamine to said at least one glycosaminoglycan is in the range of 1:1 to 20:1 w/w, said particle in the form of a sphere being capable of stably encapsulating drugs or other active ingredients that are soluble in water.

2. The water-insoluble lipidated glycosaminoglycan particle according to claim 1, wherein the glycosaminoglycan is selected from the group consisting of hyaluronic acid, keratan sulfate, chondroitin sulfate, heparin sulfate, heparan sulfate, dermatin sulfate, salts, and mixtures thereof.

3. The water-insoluble lipidated glycosaminoglycan particle according to claim 1, wherein the glycosaminoglycan is hyaluronic acid.

4. The water-insoluble lipidated glycosaminoglycan particle according to claim 1, wherein the particle size ranges from about 2-5 microns.

5. The water-insoluble lipidated glycosaminoglycan particle according to claim 1, wherein the particle size ranges from about 50-200 nanometers.

6. The water-insoluble lipidated glycosaminoglycan particle according to claim 1, wherein a water soluble active ingredient is encapsulated within the particle.

7. The water-insoluble lipidated glycosaminoglycan particle according to claim 6, wherein the water soluble active ingredient is selected from the group consisting of anti-infective agents, chemotherapeutic agents, proteins, hormones, enzymes, cells, and nucleic acids.

8. The water-insoluble lipidated glycosaminoglycan particle according to claim 7, wherein the active ingredient is a chemotherapeutic agent for treating cancer.

9. A method for preparing the water-insoluble lipidated glycosaminoglycan particle of claim 1, comprising reacting at least one glycosaminoglycan with a lipid consisting of a phosphatidylethanolamine, wherein the ratio of said phosphatidylethanolamine to said at least one glycosaminoglycan is in the ratio of 1:1 to 20:1 w/w.

10. The method according to claim 9, wherein the glycosaminoglycan is selected from the group consisting of hyaluronic acid, keratan sulfate, chondroitin sulfate, heparin sulfate, heparan sulfate, dermatin sulfate, salts, and mixtures thereof.

11. The method according to claim 10, wherein the glycosaminoglycan is hyaluronic acid.

12. A method for making the water-insoluble lipidated glycosaminoglycan particle of claim 6 having a water soluble active ingredient encapsulated within, comprising reconstituting a lyophilized lipidated glycosaminoglycan particle in water, and adding a powdered water soluble active ingredient, whereby the water soluble active ingredient is encapsulated within the water-insoluble lipidated glycosaminoglycan particle.

13. The water-insoluble lipidated glycosaminoglycan particle of claim 1 encapsulating a marker used in imaging.

14. The water-insoluble lipidated glycosaminoglycan particle according to claim 13, wherein the marker is a radioactive isotope.

15. The water-insoluble lipidated glycosaminoglycan particle according to claim 14, wherein the radioactive isotope is selected from the group consisting of $^{99}$Tc, $^{125}$I and $^{67}$Gd.

16. The water-insoluble lipidated glycosaminoglycan particle according to claim 13, wherein the marker is a fluorescent molecule.

17. The water-insoluble lipidated glycosaminoglycan particle according to claim 7, wherein the water soluble active ingredient is a nucleic acid.

18. A scaffold for tissue engineering, comprising the water-insoluble lipidated glycosaminoglycan particle of claim 1 encapsulating a whole cell.

19. The water-insoluble lipidated glycosaminoglycan particle of claim 1, wherein the ratio of said phosphatidylethanolamine to said at least one glycosaminoglycan is in the range of 5:1 to 20:1 w/w.

* * * * *